(12) United States Patent
Perry et al.

(10) Patent No.: US 8,286,845 B2
(45) Date of Patent: Oct. 16, 2012

(54) FULL THICKNESS RESECTION DEVICE CONTROL HANDLE

(75) Inventors: Stephen J. Perry, Shirley, MA (US); Paul DiCesare, Easton, CT (US); Patrick Gutelius, Monroe, CT (US); Mark Monroe, Holliston, MA (US); Jeffrey Radziunas, Wallingford, CT (US); Roy H. Sullivan, Millville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2371 days.

(21) Appl. No.: 10/964,007

(22) Filed: Oct. 12, 2004

(65) Prior Publication Data
US 2005/0125009 A1 Jun. 9, 2005

Related U.S. Application Data

(60) Division of application No. 09/957,901, filed on Sep. 20, 2001, now Pat. No. 6,821,282, which is a continuation-in-part of application No. 09/722,026, filed on Nov. 27, 2000, now Pat. No. 6,520,971.

(51) Int. Cl.
*B27F 7/00* (2006.01)

(52) U.S. Cl. ........................................ 227/175.1; 227/19

(58) Field of Classification Search ............... 227/175.1, 227/19
See application file for complete search history.

(56) References Cited

U.S. PATENT DOCUMENTS

| | | | | |
|---|---|---|---|---|
| 3,662,939 A | * | 5/1972 | Bryan | 227/19 |
| 4,728,020 A | * | 3/1988 | Green et al. | 227/19 |
| 5,271,543 A | * | 12/1993 | Grant et al. | 227/179.1 |
| 5,312,024 A | * | 5/1994 | Grant et al. | 227/179.1 |
| 5,433,721 A | * | 7/1995 | Hooven et al. | 606/143 |
| 5,439,156 A | * | 8/1995 | Grant et al. | 227/179.1 |
| 5,609,285 A | * | 3/1997 | Grant et al. | 227/179.1 |
| 6,119,913 A | * | 9/2000 | Adams et al. | 227/176.1 |
| 6,126,058 A | * | 10/2000 | Adams et al. | 227/180.1 |

* cited by examiner

*Primary Examiner* — Brian D Nash
(74) *Attorney, Agent, or Firm* — Fay Kaplun & Marcin, LLP

(57) ABSTRACT

A control mechanism for a resectioning device, comprises a first actuator coupled to a flexible drive shaft for actuating a first mechanism when operated in a first direction and for actuating, when operated in a second direction, a second mechanism and a first lockout mechanism coupled to the first actuator for preventing actuation of the first actuator in the second direction before a predetermined amount of actuation in the first direction has been completed. Furthermore, mechanisms are provided to control the release during operation in a second direction of torsional energy stored in a flexible drive shaft during operation in a first direction.

24 Claims, 24 Drawing Sheets

FULL THICKNESS RESECTION DEVICE CONTROL HANDLE

This Application is a Divisional of U.S. patent application Ser. No. 09/957,901 (issued as U.S. Pat. No. 6,821,282) filed Sep. 20, 2001, which is a Continuation-in-Part of U.S. patent application Ser. No. 09/722,026 (issued as U.S. Pat. No. 6,520,971) filed Nov. 27, 2000. The entire disclosures of these prior applications are considered part of the disclosure of the accompanying application and are hereby expressly incorporated by reference herein.

FIELD OF THE INVENTION

The present invention relates generally to a full thickness resection device. More specifically, the invention provides a device and method for controlling a full thickness resection device.

BACKGROUND INFORMATION

Known resection devices have been employed to staple and cut tissue surrounding a lesion site to remove lesions from patients' bodies. A known resection device for performing resection procedures endoscopically through naturally occurring body orifices has included a flexible portion extending from an operating end, or distal end, of the device, which is inserted into the patient's body, to a control end, or proximal end, of the device, which remains outside of the patient's body. The control end may include a control handle which may be manipulated to control cutting and stapling apparatuses of the device.

In order to maintain flexibility of that portion of the device extending between the control handle and the distal end, these resection devices have employed flexible drive shafts to transmit an actuating force from the control handle to the distal end of the device. However, as such a flexible drive shaft is rotated in the first direction to operate the stapling mechanism, torsional energy is stored therein. When the force driving the drive shaft in the first direction is removed, the stored torsional energy may urge the drive shaft to rotate in the second direction, actuating the cutting mechanism, before such a rotation is desired.

SUMMARY OF THE INVENTION

The present invention is directed to a control mechanism for a resectioning device, comprises a first actuator coupled to a flexible drive shaft for actuating a first mechanism when operated in a first direction and for actuating, when operated in a second direction, a second mechanism and a first lockout mechanism coupled to the first actuator for preventing actuation of the first actuator in the second direction before a predetermined amount of actuation in the first direction has been completed. Furthermore, mechanisms are provided to control the release during operation in a second direction of torsional energy stored in a flexible drive shaft during operation in a first direction and to prevent mistaken operation of resectioning mechanisms by locking out a first actuator whenever a second actuator is operable.

BRIEF DESCRIPTION OF THE DRAWINGS

The various features of the invention will best be appreciated by simultaneous reference to the description which follows and the accompanying drawings, in which.

DETAILED DESCRIPTION OF INVENTION

Figure 1:
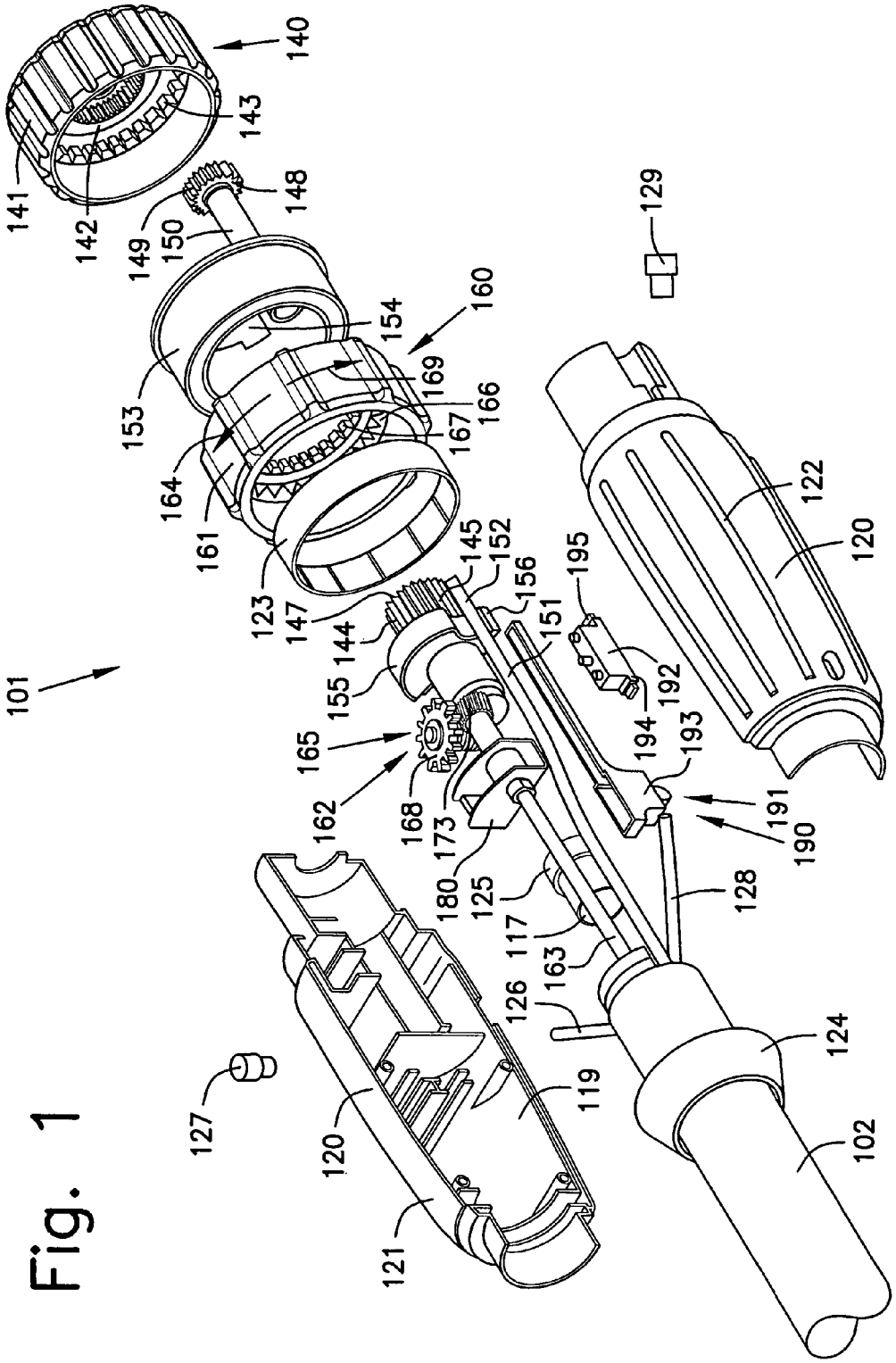
FIG. 1 is an exploded perspective view of a first embodiment of a full thickness resection device control handle in accordance with the present invention.

FIGS. 1 through 13 illustrate a first embodiment for the components of control handle 101 of the present invention. As can be seen, control handle 101 includes body 120, clamping or gap adjust assembly 140, resectioning assembly 160, and locking assembly 190. Each of these components will be discussed in further detail below.

Control handle 101 is disposed at a proximal end of a full thickness resection device (i.e., an end of the device which, during operation, remains, outside the body of a patient).

Flexible tube 102 extends from control handle 101 to a distal end of the full thickness resection device which includes the cutting and stapling apparatuses and which is inserted into the body of a patient. The construction and operation of a full thickness resectioning device is described in more detail in U.S. application Ser. No. 09/100,393 which is expressly incorporated herein by reference in its entirety.

As will be further described later in this specification, a gap adjust assembly 140 activates mechanisms for adjusting the size of a gap between a staple head and anvil head of the stapling apparatus in the distal end of the device. Resectioning assembly 160 actuates both the stapling apparatus and a cutting apparatus which is also located at the distal end of the full thickness resection device.

As mentioned above, control handle 101 includes a body 120 including a first handle half 121 and a second handle half 122. As can be seen in FIG. 1, the internal structure of body 120 may preferably include molded support framing 119 which supports the components disposed therewithin. The first handle half 121 is joined to the second handle half 122 with the components included within the body 120 disposed therebetween. A circular handle clamp ring 123 is mounted around proximal ends of the first and second handle halves 121 and 122, respectively, and assists in maintaining the joined configuration for the first and second handle halves 121 and 122, respectively. Similarly, nose ring 124 is disposed around the distal ends of first and second handle halves 121, 122, respectively, and also assists in maintaining the joined configuration for the first and second handle halves, 121 and 122, respectively.

Scope seal 125 is disposed within body 120 and is maintained in its position therewithin by support framing 119 with scope seal 125 defining an aperture 117 therethrough. When in an operative configuration, an endoscope (not shown) extends through the control handle 101 as will be described below passing through the aperture 117, to pass through a flexible tube 102 to the distal end of the full thickness resection device. A distal end of the scope seal 125 forms a tube that extends through a portion of the flexible tube 102. Thus, in the operative configuration, an endoscope extends through the tube of the scope seal 125 into the flexible tube 102. The purpose of the scope seal 125 is to provide a seal around the endoscope such that if, for example, an organ into which the full thickness resectioning device is inserted is insufflated, the increased air pressure is sealed within the tube 102 and prevented from escaping through the control handle 101.

Also included in body 120 are first and second grasper tubes 126 and 128, each of which provides a lumen through which a separate devices (e.g., a grasper device or schlerotherapy needle) may be inserted into the tube 102. The first grasper tube 126 extends through an opening 115 in the first handle half 121 while the second grasper tube 128 extends through a second opening 115 in the second handle half 122. A first grasper seal 127 is positioned around the first grasper tube 126 outside of the first handle half 121 to seal the corresponding opening 115 while a second grasper seal 129 is similarly positioned around the second grasper tube 128 outside the second handle half 122 to seal the corresponding opening 115. The grasper seals 127, 129 provide a close fit around the device inserted through the respective grasper tube 126, 128 to prevent materials from passing out of the proximal ends thereof.

A description will now be provided of gap adjust assembly 140. As described above, gap adjust assembly 140 allows a user to adjust the size of a gap between a staple head and an anvil head of a stapling device located at the distal end of the full thickness resection device. The gap may be adjusted, for example, to clamp a portion of tissue to be stapled there before actuating the stapling device. The gap adjust assembly 140 includes a gap adjust ring 141 which may, for example be formed as a knob, a clamp shaft gear 144, a spur gear 148, a gap adjust flexible drive shaft 151, a transition piece 153, and a follower 155. Each of these components will be described in further detail below.

The gap adjust ring 141 is a circular structure having an aperture extending therethrough through which, as discussed previously, an endoscope may be inserted into the control handle 101. The gap adjust ring 141 is rotatably mounted on the body 120 and includes gear teeth 142 on an inner portion thereof. As will be further described, gear teeth 142 engage gear teeth 145 formed on the clamp shaft gear 144. The gap adjust ring 141 also includes cog teeth 143 formed on an inner portion thereof As will also be described later in this specification, cog teeth 143 which mesh with a corresponding structure of a locking assembly 190 to prevent the gap adjust ring 141 from being rotated when the locking assembly 190 is received therewithin.

Figure 2:
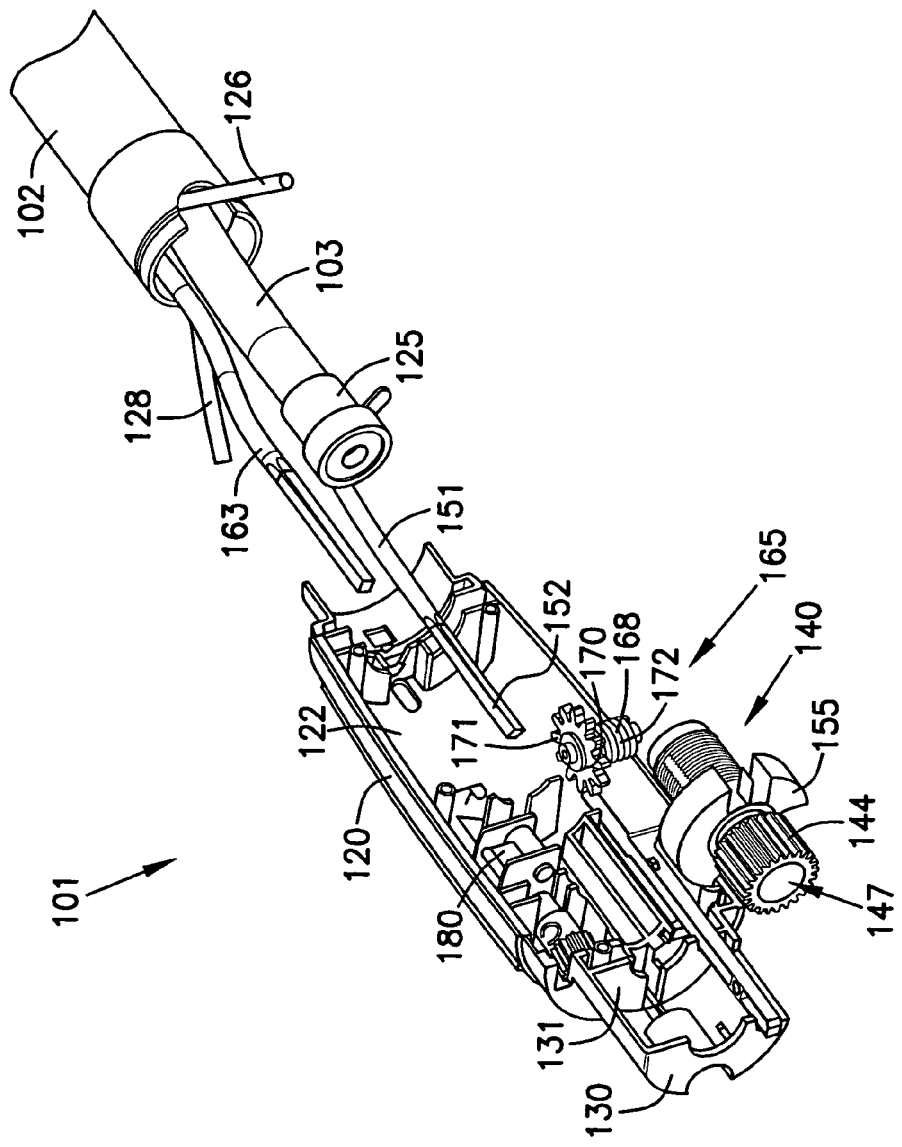
FIG. 2 is an exploded perspective view of a portion of the control handle of FIG. 1.
Figure 3:
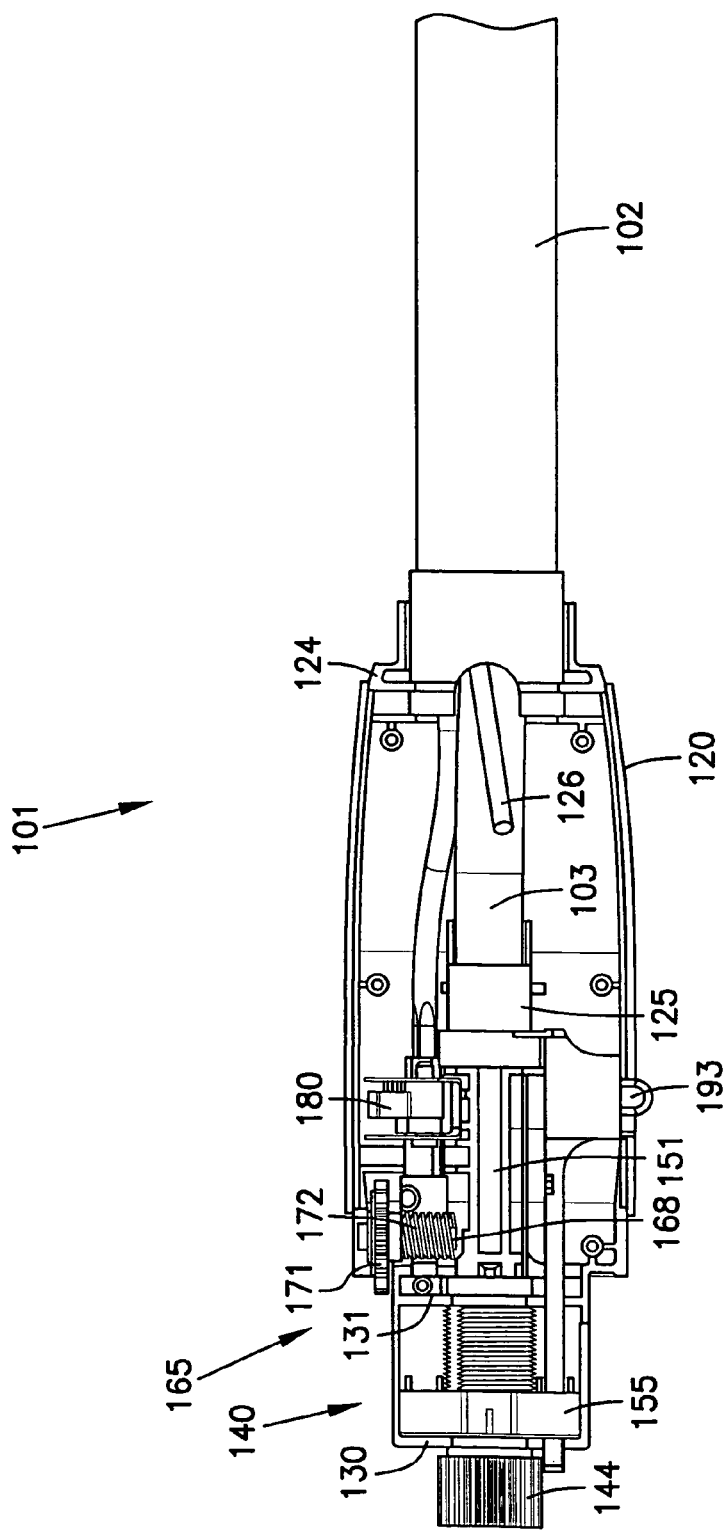
FIG. 3 is a cross-sectional view of the embodiment of FIG. 2.

As shown more clearly in FIGS. 1-3, gear teeth 145 of clamp shaft gear 144 engage gear teeth 142 of gap adjust ring 141 so that, as gap adjust ring 141 is rotated, the gear teeth 142 rotate clamp shaft gear 144. The clamp shaft gear 144 also defines an aperture 147 therethrough through which an endoscope may be inserted. Clamp shaft gear 144 also engages spur gear 148 as gear teeth 145 mesh with gear teeth 149 of spur gear 148. Thus, as gap adjust ring 141 rotates clamp shaft gear 144, clamp shaft gear 144 in-turn rotates spur gear 148. Spur gear 148 is not directly driven by gap adjust ring 141. Rather, spur gear 148 is indirectly driven by gap adjust ring 141 through rotation of clamp shaft gear 144 by gap adjust ring 141. This gearing mechanism for gap adjust assembly 140 permits the positioning of the endoscope through a centerline of the control handle 101 by offsetting the spur gear 148 and allows a designer to select a desired drive ratio for gap adjust ring 141.

A shaft 150 is coupled to the spur gear 148 and extends through and is supported by an opening 154 defined by a transition piece 153 so that the spur gear 148 may rotate within the opening 154. The distal end of the shaft 150 of the spur gear 148 is connected to a proximal end of a gap adjust flexible drive shaft 151 which extends to the distal end of the full thickness resectioning device. The proximal end 152 of the drive shaft 151 is positioned within a scallop 156 which extends from a follower 155. Scallop 156 allows for rotation of the drive shaft 151 while supporting the proximal end thereof. As the spur gear 148 is rotated by the clamp shaft gear 144, the drive shaft 151 is also rotated due to a torsionally rigid attachment between the drive shaft 151 and the spur gear 148.

The gap adjust drive shaft 151 is preferably formed as a longitudinally flexible, substantially torsionally rigid shaft. However, in practice such a flexible drive shaft will store torsional energy therewithin it as it is rotated. Rotation of drive shaft 151 translationally moves the at least one of the anvil and stapling heads with respect to the other to adjust the stapling gap therebetween.

Figure 4:
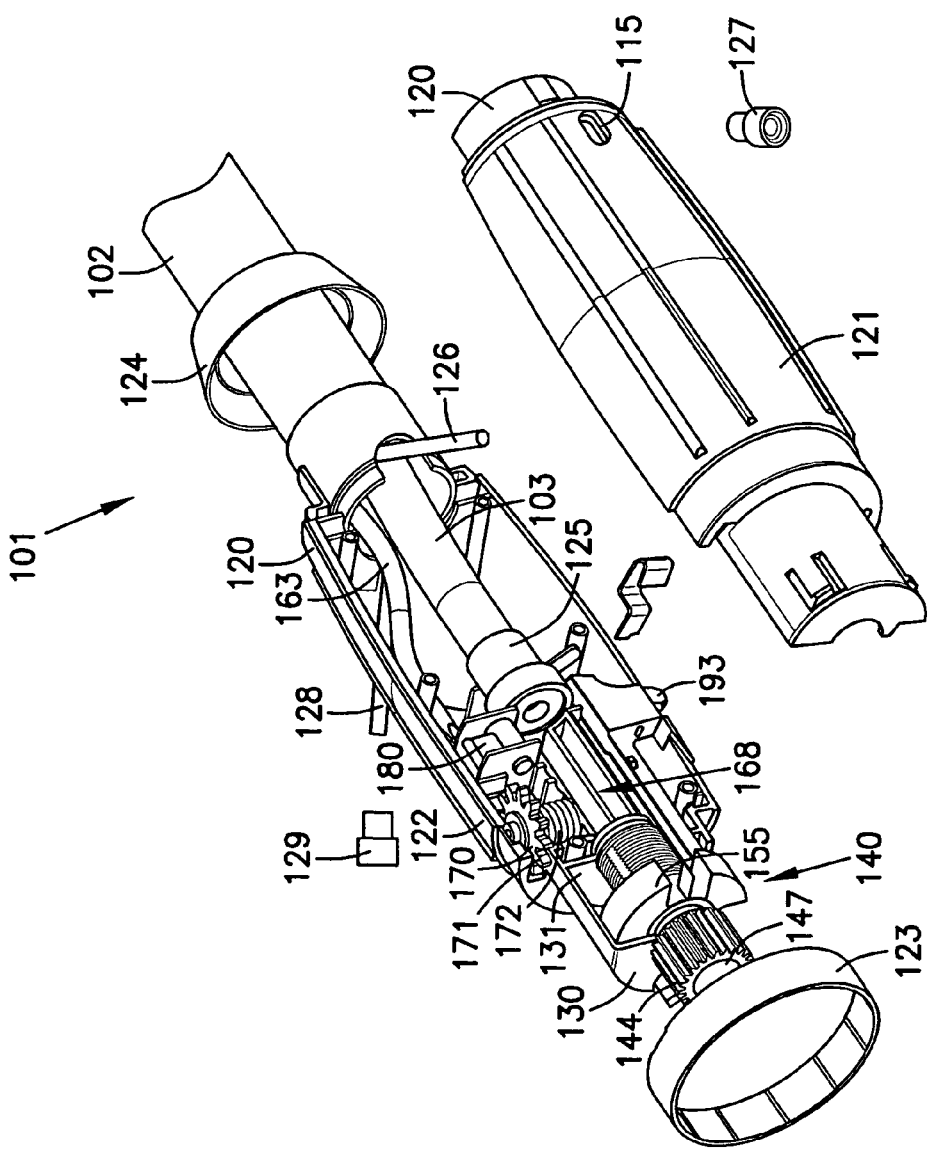
FIG. 4 is an exploded perspective view of a portion of the control handle of FIG. 1.
Figure 5:
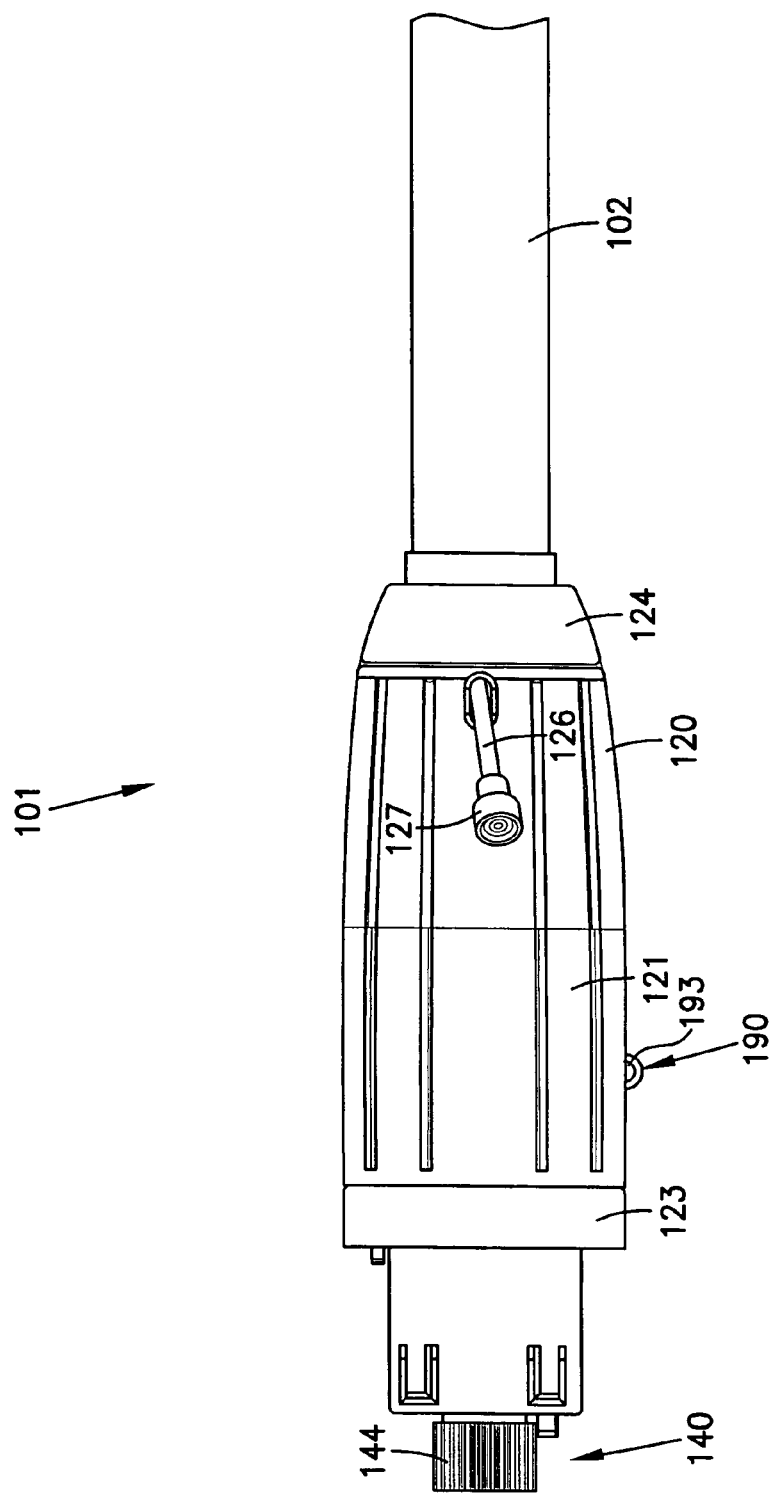
FIG. 5 is a perspective view of the portion of the control handle of FIG. 4.

The follower 155 which is movably disposed on clamp shaft gear 144 includes an internal threaded portion that engages a threaded shaft 146 included on the clamp shaft gear 144. Thus, for example, as clamp shaft gear 144 is rotated clockwise (when viewed from the proximal end of the control handle 101), the follower 155 moves proximally on clamp shaft gear 144. Conversely, as the clamp shaft gear 144 is rotated counter-clockwise, the follower 155 will move distally on clamp shaft gear 144. As shown in FIGS. 2-4, the proximal and distal motion of the follower 155 on clamp shaft gear 144 is limited by stops 130, 131 formed by body 120. Thus, the position of stops 130, 131 and that of the follower 155 are preferably selected prevent adjustment of the stapling gap outside a desired range. That is, over-rotation of gap adjust ring 141 in either direction is prevented and no rotation may be imparted to the gap adjust drive shaft 151 beyond the desired limits. As would be understood by those of skill in the art, after the gap adjust ring 141 has been rotated to either completely extend the gap between the anvil head and staple firing head to a maximum desired distance or to reduce the gap to a minimum desired distance, the torsional energy which may have been stored within the gap adjust drive shaft 151 may be release so that a further rotation is imparted to a distal end thereof. Thus, this additional rotation due to stored torsional energy should preferably be taken into account when setting the position of the stops 130 and 131.

As described in more detail below, a control mechanism for a resectioning device according to the present invention comprises a first actuator coupled to a flexible drive shaft for actuating a first mechanism when operated in a first direction and for actuating, when operated in a second direction, a second mechanism and a first lockout mechanism coupled to the first actuator for preventing actuation of the first actuator in the second direction before a predetermined amount of actuation in the first direction has been completed. For example, the resection activating mechanism 161 may serve as a first actuator for actuating a first mechanism (e.g., a staple driving mechanism) when rotated in a first direction while actuating a second mechanism (e.g., a tissue cutting mechanism) when rotated in a second direction. As discussed previously, the control handle 101 also includes a resectioning assembly 160 which is utilized to fire staples from the stapling head at the distal end of the full thickness resection device. Resectioning assembly 160 includes a resection activating mechanism 161 which may be, for example, a staple firing ring or staple-cut ring, a controlling device 162, a flexible drive shaft 163, and a staple-cutting lockout mechanism 180 which may be, for example, a ratchet assembly as shown in FIG. 1. The resection activating mechanism 161 is coupled to and drives the flexible drive shaft 163 to drive the staple-cutting lockout mechanism 180. The controlling device 162 engages the flexible drive shaft 163 to control a dissipation of torsional energy built up in the flexible drive shaft 163 during the driving of the flexible drive shaft 163 by the resection activating mechanism 161 in a first direction 164. First direction 164 may be either clockwise or counterclockwise, for a first operative procedure or mode, such as tissue stapling with the opposite direction of rotation being employed for another operation (e.g., tissue cutting). Those skilled in the art will understand that there are a variety of configurations available for the controlling device 162 which will achieve the goals of the invention. In the exemplary embodiment, the controlling device 162 is formed of a worm gear assembly 165 which couples the resection activating mechanism 161 to the flexible drive shaft 163. Each of these components will be described in further detail below.

The resection activating mechanism 161 is rotatably mounted on the body 120 and includes gear teeth 166 formed on a distal, inner portion thereof In this embodiment, the resection activating mechanism 161 and the gap adjust ring 141 are concentrically aligned with respect to one another. Although the rings 141 and 161 may be positioned on body 120 in a variety of ways, this concentric positioning of the rings 141 and 161 on the body 120 allows an endoscope to be passed through the center of the control handle 101, and permits a user to utilize the control handle 101 and access all the required controls regardless of the orientation of the control handle 101 around the endoscope.

As will be further described below, resection activating mechanism 161 includes the gear teeth 166 which engage the worm gear assembly 165 as well as cog teeth 167 formed on a proximal, inner portion thereof. The cog teeth 167 receive therewithin the locking assembly 190 in order to lock the resection activating mechanism 161 in position and prevent undesired rotation thereof.

As mentioned above, and as shown in FIG. 10, the controlling device 162 may include a worm gear assembly 165 coupling the resection activating mechanism 161 to the flexible drive shaft 163. In a first operative mode the worm gear assembly 165 may be actuated by rotation of the resection activating mechanism 161 in a first 164 to rotate the flexible drive shaft 163 in the first direction 164. Furthermore, the worm gear assembly 165 may be actuated in a second operative mode, to rotate in a second direction 169 when the resection activating mechanism is rotated in the second direction 169. This causes a corresponding rotation of the flexible drive shaft 163 in the second direction 169, opposite to the first direction 164. Under the second operative mode, the drive shaft 163 rotates in the second direction 169 (counterclockwise) to actuate, for example, a second operative procedure (e.g., tissue cutting), by causing a corresponding action of a tissue cutting mechanism located at a distal end of the full thickness resection device. At the beginning of the second operative mode, a release rate of the torsional energy stored in the flexible drive shaft 163, as a result of the previous rotation of the drive shaft 163 in the first direction 164, is controlled by actuation of the worm gear assembly 165 in the second operative mode.

Figure 12:
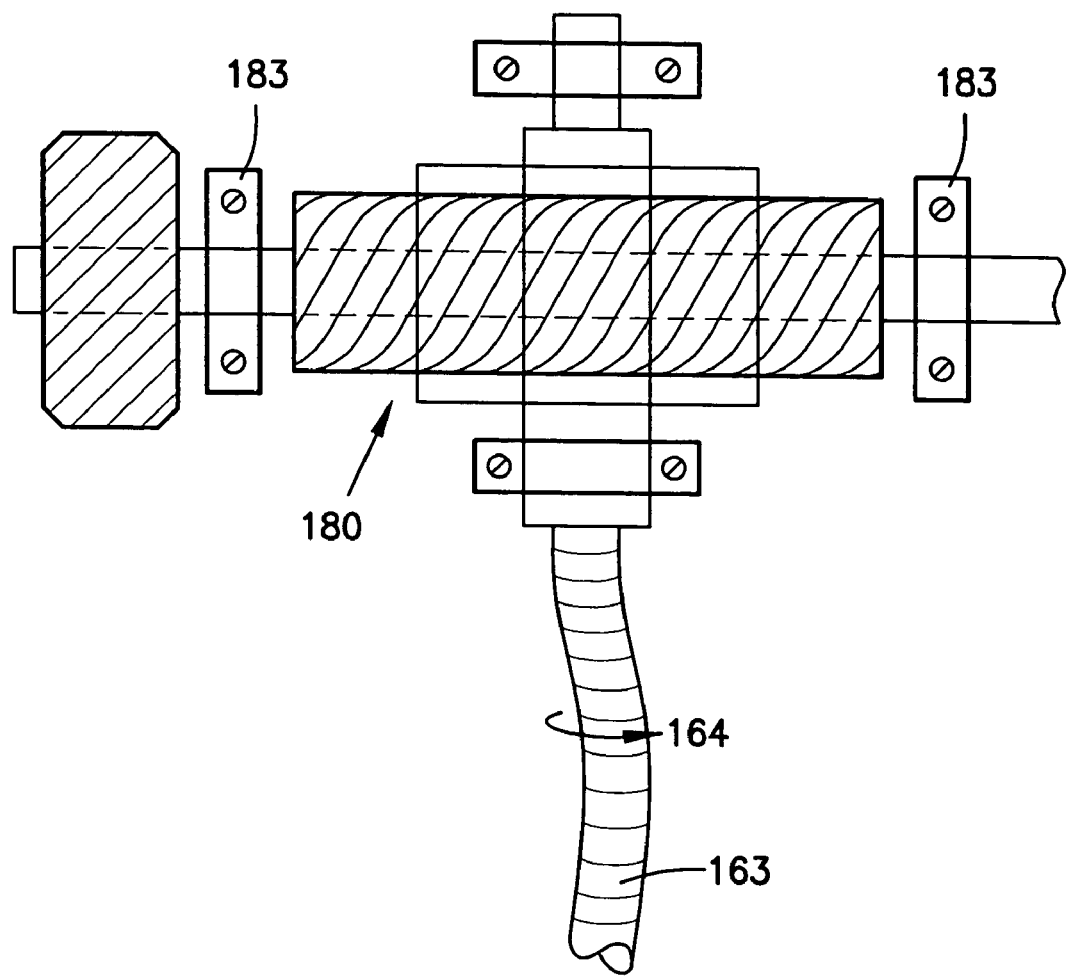
FIG. 12 is a second schematic illustration of the worm gear assembly of the embodiment of FIG. 1, as viewed from a front of the assembly.
Figure 13:
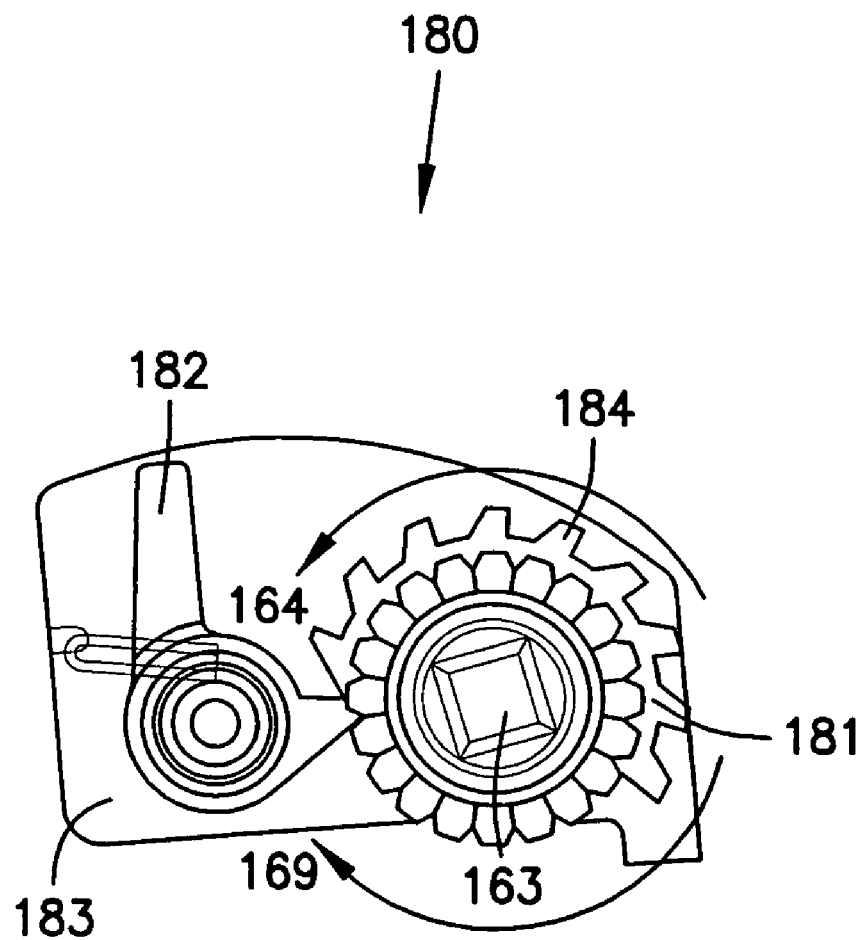
FIG. 13 is a cross-sectional view of the ratchet assembly of the embodiment of FIG. 1.

Actuation of the worm gear assembly 165 in the second operative mode may be accomplished by either active rotation, i.e., rotation by the user of the resection activating mechanism 161 in the second direction 169 or by simply removing a force from resection activating mechanism 161 that restrains it from rotating in the second direction 169. In other words, as the flexible drive shaft 163 has torsional energy stored therewithin as a result of the rotation in the first direction 164, it is biased to rotate in the second direction 169 unless restrained there against, as shown in FIG. 12. When the restraining force is removed from resection activating mechanism 161, the flexible drive shaft 163 may rotate in the second direction but will not uncontrollably rotate due to a desirably inefficient transfer of energy resulting from the worm gear assembly 165, as will be further discussed.

Figure 10:
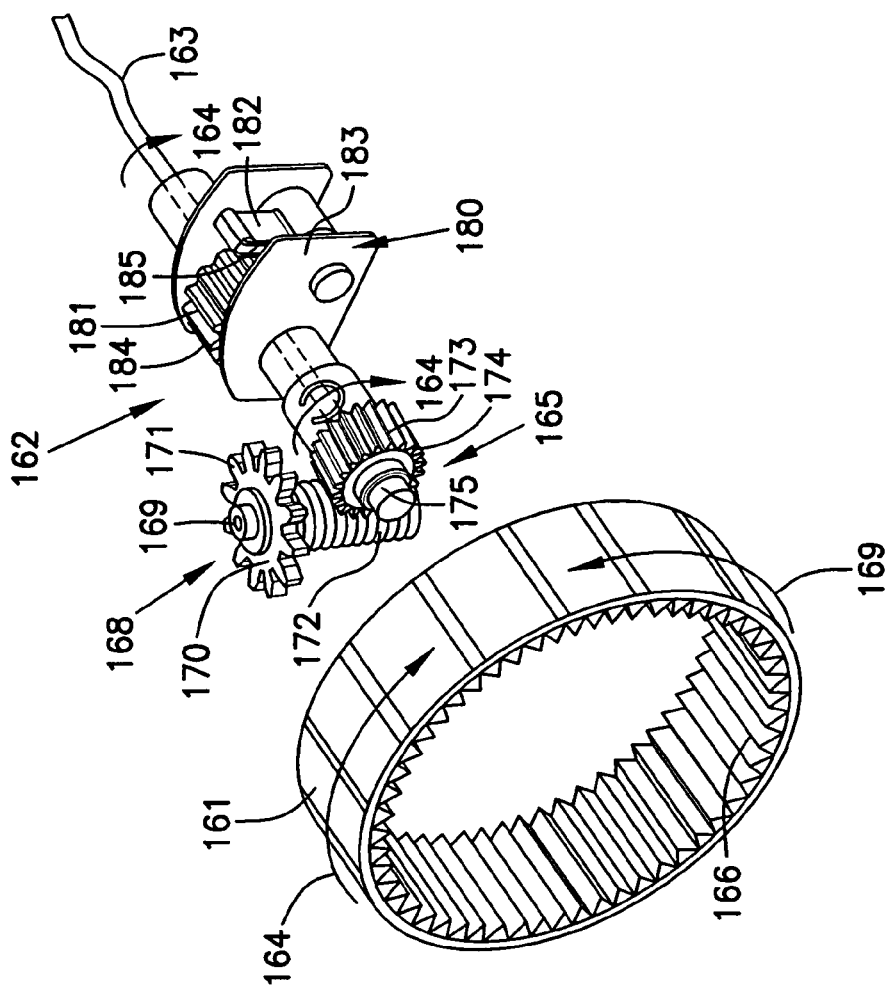
FIG. 10 is an exploded perspective view of a portion of the control handle of FIG. 1.

As shown in FIGS. 1 through 4, and in more detail in FIG. 10, worm gear assembly 165 includes a worm pinion 168 and a worm gear coupling 173. The worm pinion 168 includes a top side 170 with gear teeth 171 thereon and a stem portion 172 which includes threading along its length. The gear teeth on the top side 170 of the worm pinion 168 engage gear teeth 166 of the resection activating mechanism 161. Thus, rotation of the resection activating mechanism 161 causes a corresponding rotation of the worm pinion 168.

When the resection activating mechanism 161 is rotated in the first direction 164 during the first operative mode, in order to fire the staples from the stapling mechanism in the distal end of the full thickness section device, the top side 170 of the worm pinion 168 is rotated in the second direction 169 (counter-clockwise) when viewed from above in FIG. 10. The rotation of the top side 170 of the worm pinion 168 in the second direction 169 then rotates the threaded stem portion 172 of the worm pinion 168 in the second direction 169 which engages gear teeth 174 of the worm gear coupling 173 to rotate the worm gear coupling 173 in the first direction 164 (clockwise when viewed from the proximal end of control handle 101).

As the flexible drive shaft 163 is attached at its proximal end 175 to the worm gear coupling 173, rotation of the worm gear coupling 173 by the worm pinion 168 in the first direction 164, causes the flexible drive shaft 163 to rotate in the first direction 164. Because of the flexibility of the flexible drive shaft 163, as discussed above, torsional energy is stored therewithin during this rotation by the worm gear coupling 173. FIG. 12 illustrates the flexible drive shaft 163 after it has been rotated and with torsional energy stored therewithin as a result of the rotation.

The staple firing mechanism includes a staple-cutting lockout mechanism that does not permit a surgeon to begin tissue cutting until the device has completed the tissue stapling operation (e.g., by firing staples through an entire firing range of the stapling mechanism). In this embodiment, the staple-cutting lockout mechanism 180 includes a ratchet assembly as shown in FIG. 10 and in more detail in FIG. 13. The staple-cutting lockout mechanism 180 which is associated with the flexible drive shaft 163 includes a ratchet 181, a pawl 182 biased into contact with the ratchet 181 by a spring 185, and a ratchet/pawl cage 183. The ratchet 181 is rotatably mounted within the ratchet pawl cage 183 and the pawl 182 is coupled to the ratchet/pawl cage 183 and is engageable with the ratchet 181.

The ratchet 181 is disposed on a distal-most portion of the worm-gear coupling 173. The distal end of the worm gear coupling 173 includes a flat surface thereon and the ratchet 181 is positioned on a distal end of the worm gear coupling 173. The flat surface assists in coupling the ratchet 181 to the worm gear coupling 173 such that the ratchet 181 will rotate in the first direction 164 with the worm gear coupling 173 to drive the flexible drive shaft 163. Alternatively, ratchet 181 may be disposed on a rigid drive shaft, a distal end of which would be coupled to the flexible drive shaft 163.

The ratchet 181 includes teeth 184 for around a portion of an outer surface thereof. As the ratchet 181 is rotated in the first direction 164 through the full firing range of the resectioning assembly 160, the pawl 182 is sequentially moved into engagement with each of the teeth 184 under the previously mentioned bias and is slid along the surface of the teeth against the bias to the next tooth 184. As is known in the art, each of the teeth 184 includes a gradual extension away from a surface thereof on a first side and a substantially radial abutting surface on an opposite side thereof to allow the pawl to slide along the surface of the ratchet 181 in the first direction while preventing rotation of the ratchet 181 in the second direction. Those skilled in the art will understand that rotation through the full firing range of the stapling mechanism depends on the characteristics of the stapling mechanism utilized in the full thickness resectioning device and may, for example, correspond to an arc of rotation of the resection activating mechanism 161 necessary to completely fire all of the staples from the stapling head into the tissue surrounding the opening to be formed by removal of the tissue to be resected. Thus, the teeth 184 of the ratchet 181 may preferably be disposed around a portion of the ratchet 181 selected so that, as the ratchet 181 is rotated through the full firing range, the pawl 182 prevents the ratchet 181 from rotating in second direction 169.

The ratchet 181 and the pawl 182 function as a staple-cutting lockout mechanism preventing users from activating the tissue cutting mechanism if the staple firing sequence has not been completed, i.e., by firing less than all of the required staples by rotating the resection activating mechanism 161 partially only in the first direction 164 and then trying to rotate the resection activating mechanism 161 in the second direction 169. Such cutting before the tissue to be cut has been completely stapled may result in an opening to an exterior of the organ with possibly dire consequences.

Figure 11:
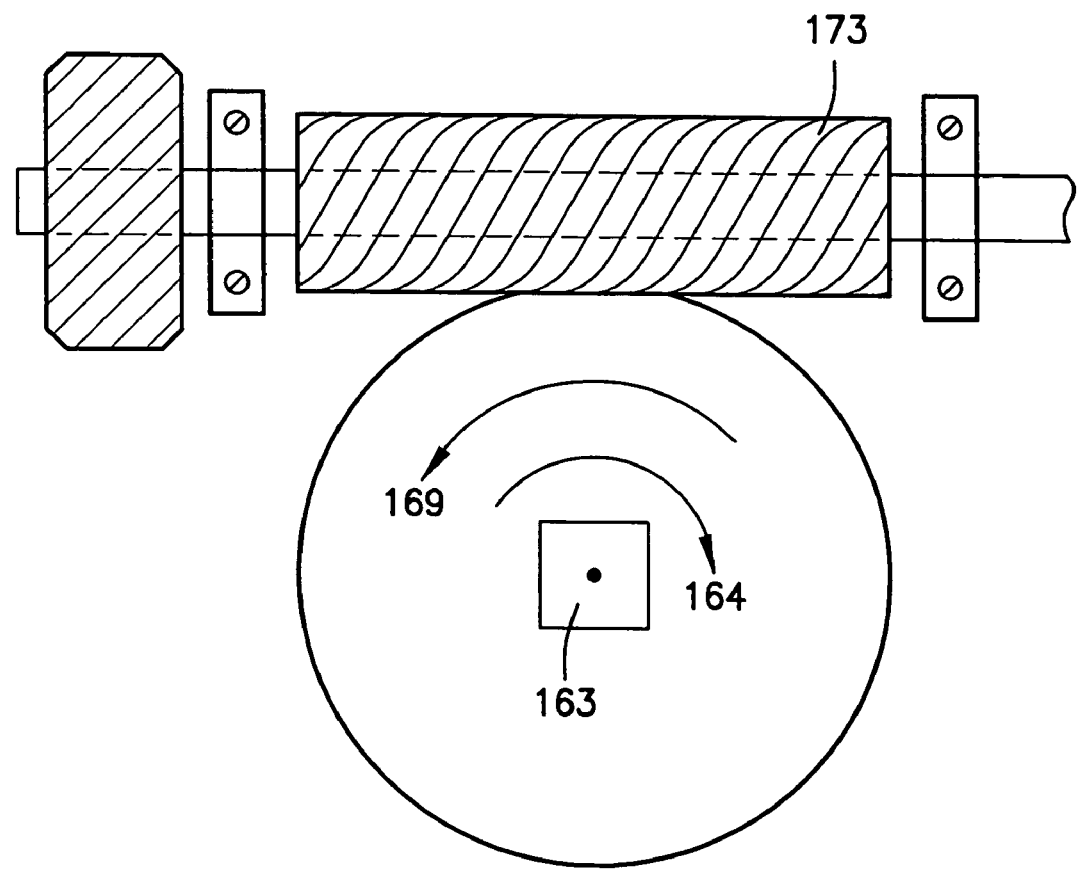
FIG. 11 is a first schematic illustration of the worm gear assembly of the embodiment of FIG. 1, as viewed from a top of the assembly.

When the staple firing procedure has been completed, i.e., the flexible drive shaft 163 has been completely rotated clockwise through the full staple firing range to fire all of the required staples, the rotation of the ratchet 181 has brought an end of the ratchet 181 past the reach of the pawl 182 so that the bias of the spring 185 rotates the pawl through the now empty space that had been occupied by the ratchet 181 so that the ratchet 181 is left free to rotate in the second direction without hindrance by the pawl 182. Thus, the ratchet 181 is configured so that it remains in contact with the pawl 182 until the proper amount of rotation in the first direction 164 has been completed and then allows the pawl 182 to rotate away from the teeth 184 of the ratchet 181. FIG. 11 illustrates the rotation of flexible drive shaft 163 in the first and second directions 164 and 169, respectively.

Furthermore, the controlling device 162 operates to prevent the torsional energy stored in the flexible drive shaft 163 during the staple firing operation from causing uncontrolled rotation of the drive shaft 163 in the second direction (and the corresponding uncontrolled tissue cutting that would result) when the staple-cutting lockout mechanism 180 disengages to permit the reverse rotation in the second direction 169. Thus, controlling device 162 provides for a controlled, gradual release of this stored torsional energy to achieve a smooth and regulated cutting action.

The control handle 101 also includes a locking mechanism 190 that alternatively locks the gap adjust assembly 140 and the resectioning assembly 160 so that only one of these mechanisms can be activated at any given time. Either gap adjust ring 141 or resection activating mechanism 161 may be rotated by the user while the other of the mechanisms is locked-out against rotation. Thus, the user may either adjust the gap or fire the staples and is not able to do both procedures simultaneously. This serves to prevent user errors which would otherwise result in the actuation of the wrong mechanism.

Those skilled in the art will understand that the locking assembly 190 may have a variety of different configurations so long as this alternative locking function is achieved. According to the embodiment shown in FIGS. 1 and 6, the locking assembly 190 includes a spring loaded pin arrangement 191 having a shuttle 192 and a button beam 193. The shuttle 192 which is slidably disposed within the transition piece 153 includes a first tab 194 and a second tab 195 which may both be extended beyond the transition piece 153 so that they are received between either the cog teeth 143 of the gap adjust ring 141 or the cog teeth 167 of the resection activating mechanism 161. A top portion of the shuttle 192 is disposed within the button beam 193 which is slidably moves the shuttle 192 within the transition piece 153 between engagement with the gap adjust ring 141 and the resection activating mechanism 161. The size of the shuttle 192 is selected so that at no time can the shuttle 192 be out of engagement with both the gap adjust ring 141 and the resection activating mechanism 161.

The control mechanism may further comprise a second actuator (e.g., gap adjust ring 141) for actuating a third mechanism (e.g., a mechanism for adjusting a gap between stapler and anvil) with the second actuator coupled to the first actuator by a second lockout mechanism described below permitting operation of only one of the first and second actuators at a given time. As discussed above, the shuttle 192 is slidably disposed within the transition piece 153. In order to lock the gap adjust ring 141 against further rotation, the user moves the button beam 193 proximally so that a locking member (e.g., the shuttle 192) is also moved proximally to abut a surface of the gap adjust ring 141. When the shuttle 192 is in the proximal position, the second tab 195 is received between the cog teeth 143 of the gap adjust ring 141 preventing rotation of the gap adjust ring 141 in either the clockwise or the counter-clockwise direction. Additionally, when the tab 195 is received between the cog teeth 143, the tab 194 is removed from the cog teeth 167 so that the resection activating mechanism 161 may be rotated by the user. By moving the button beam 193 distally, a user may lock the resection activating mechanism 161 against rotation. As the button beam 193 is moved distally, the shuttle 192 is moved distally so that the first tab 194 of the shuttle 192 is received between the cog teeth 167 of the resection activating mechanism 161 preventing rotation thereof. When tab 194 is received between the cog teeth 167, the tab 195 is removed from between the cog teeth 143 so that the gap adjust ring 141 may be rotated by the user.

Figure 6:
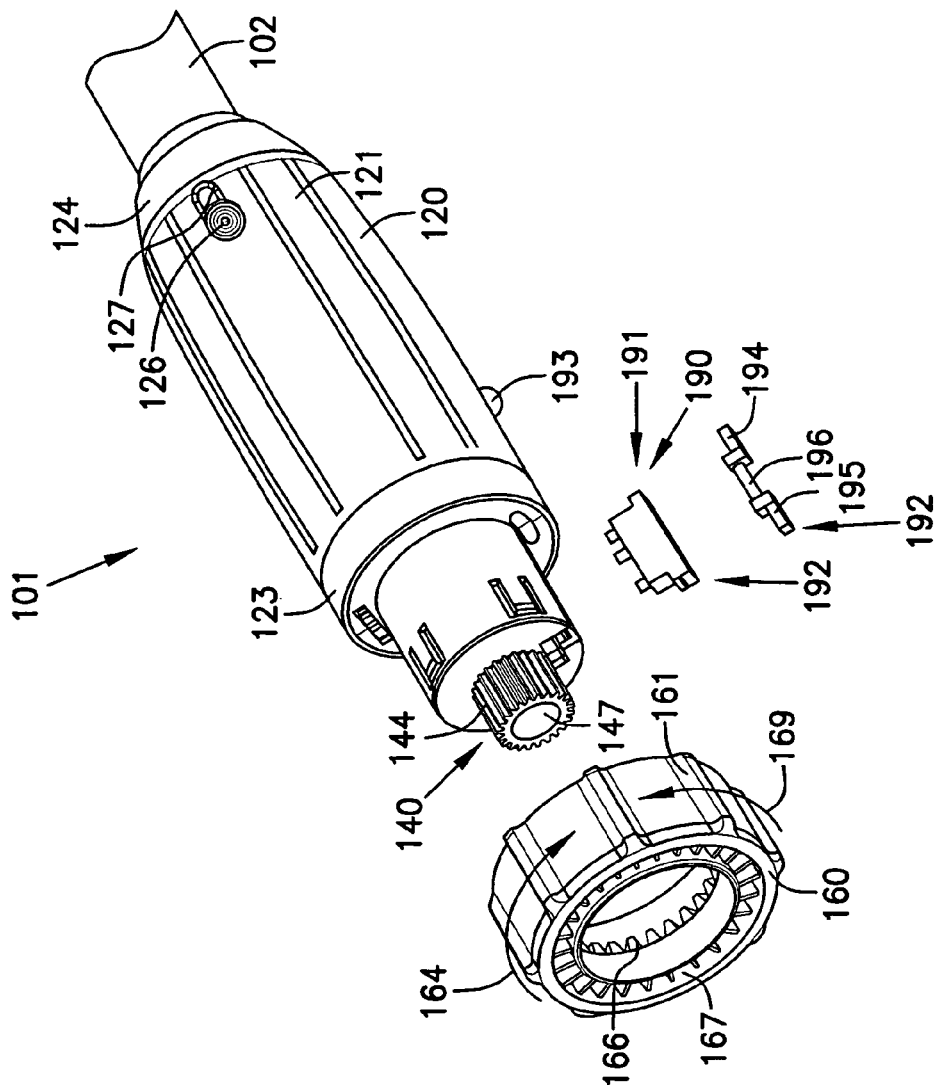
FIG. 6 is an exploded perspective view of a portion of the control handle of FIG. 1.
Figure 7:
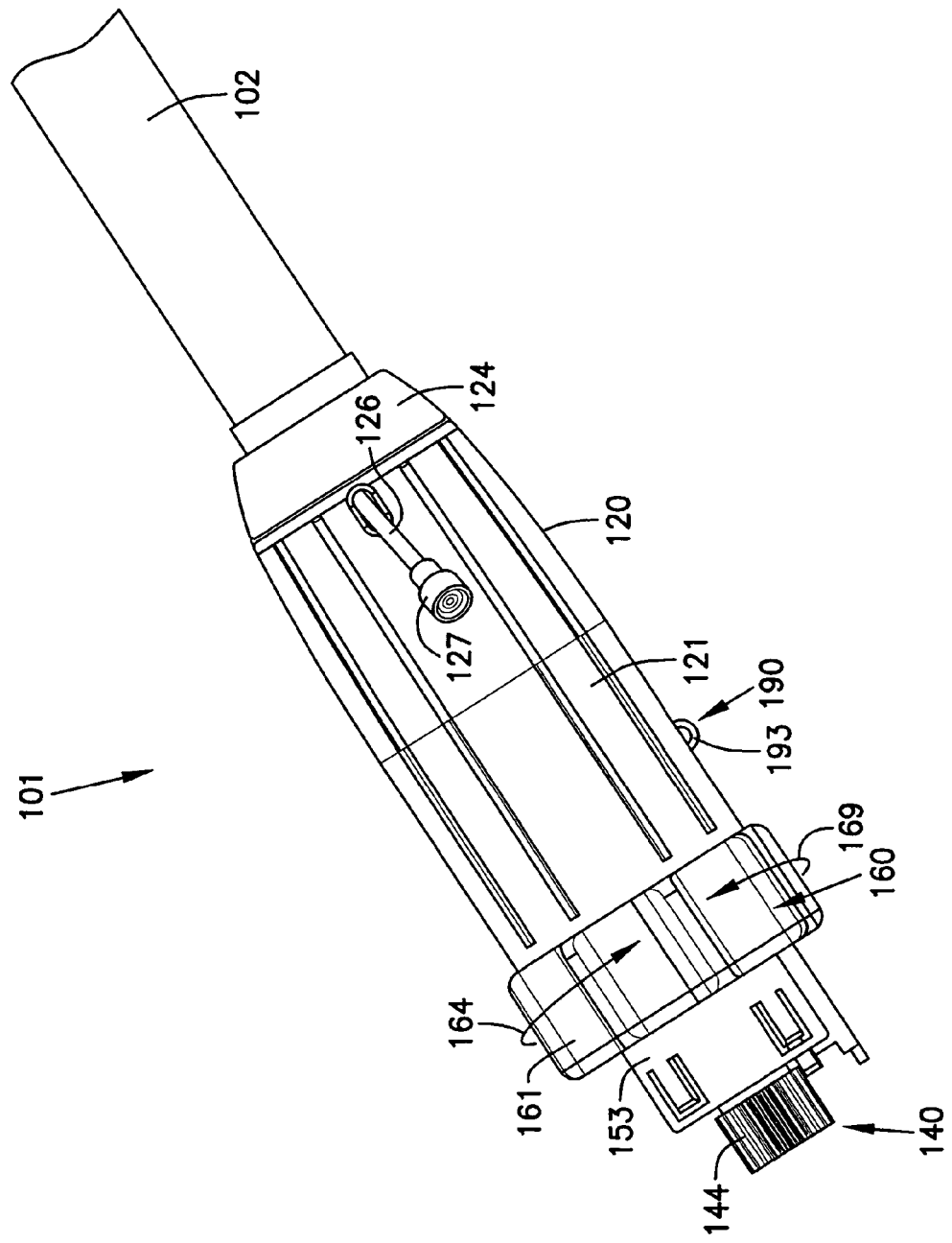
FIG. 7 is a perspective view of the portion of the control handle of FIG. 6.
Figure 8:
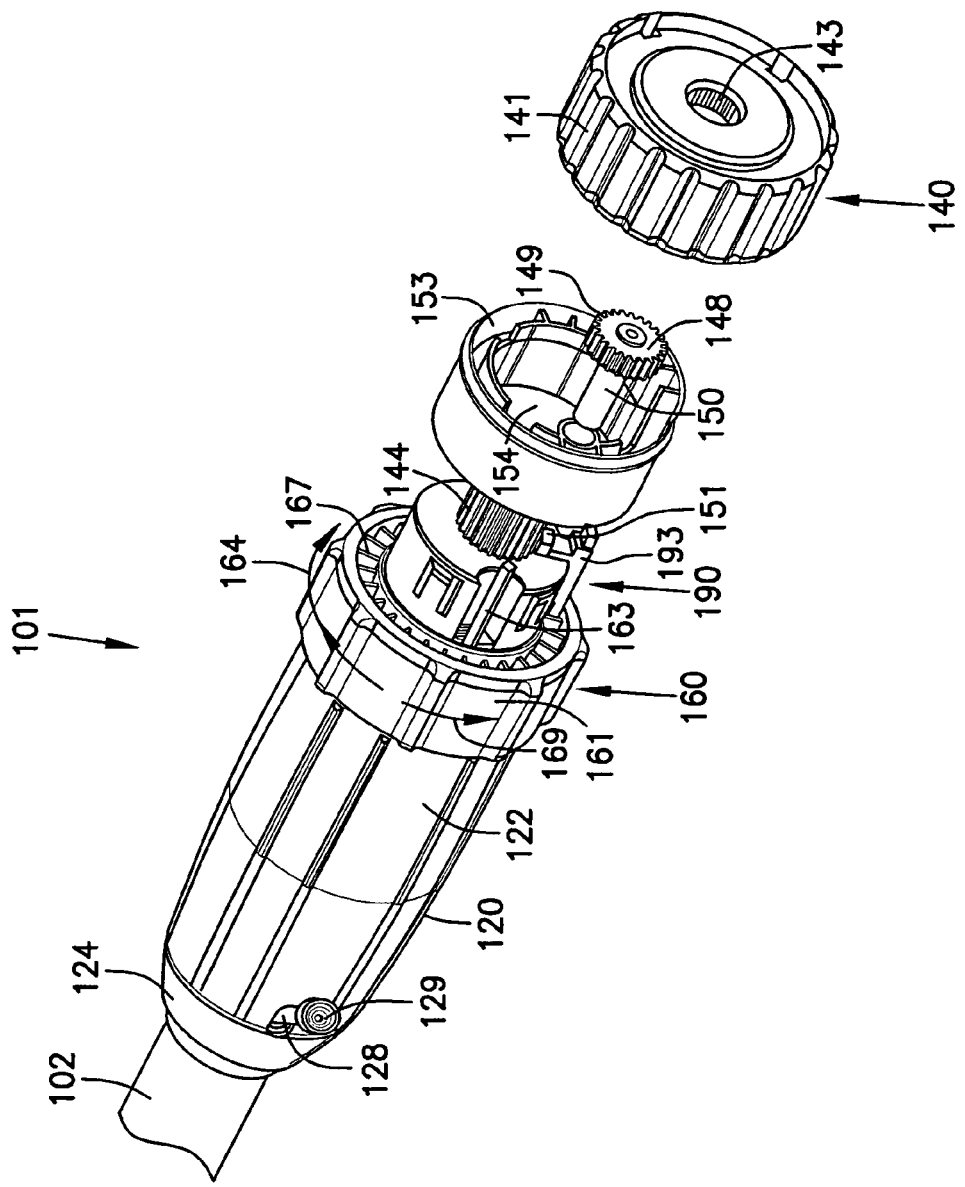
FIG. 8 is an exploded perspective view of a portion of the control handle of FIG. 1.
Figure 9:
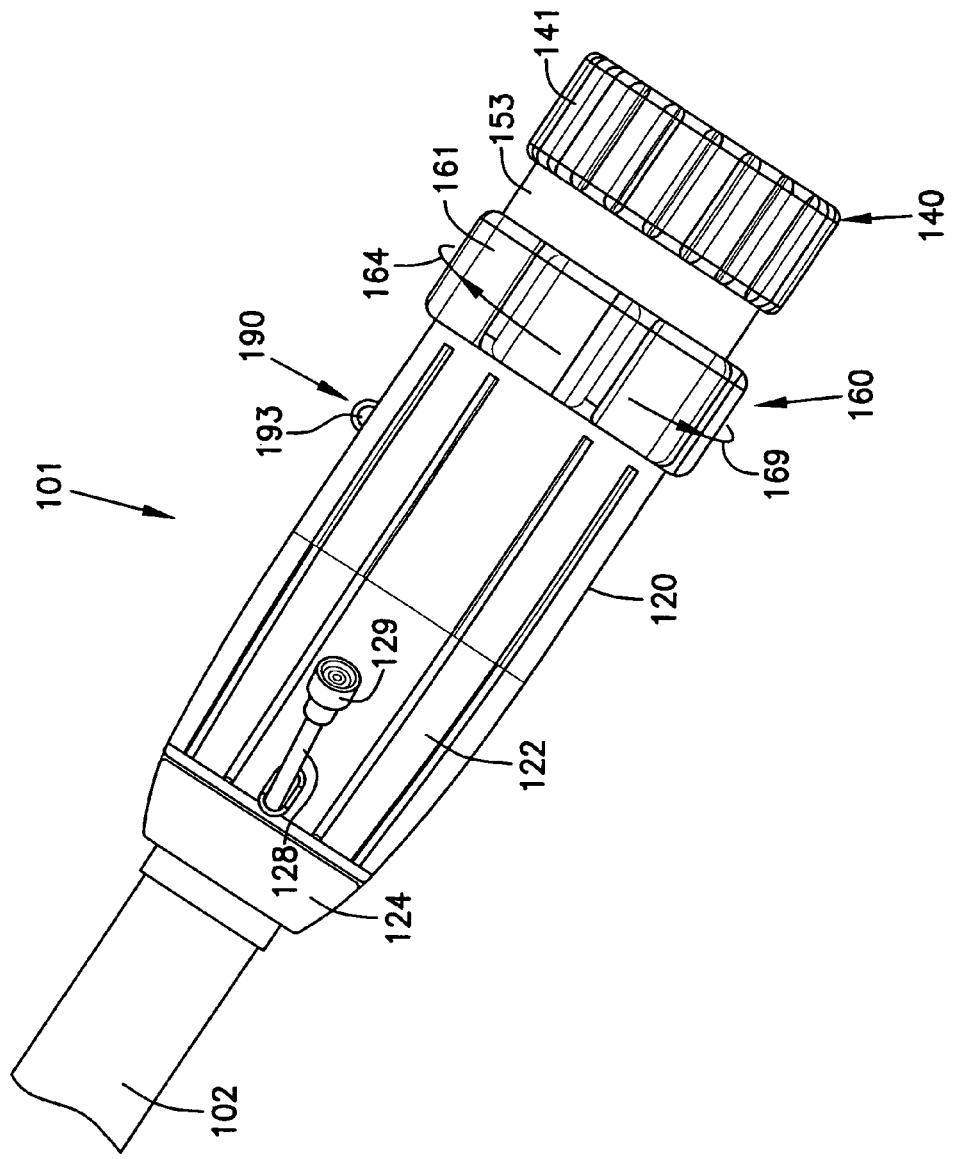
FIG. 9 is a perspective view of the portion of the control handle of FIG. 8.

As can be seen in FIG. 6, a biasing spring 196 is included within the shuttle 192 which biases both the first tab 194 and the second tab 195 radially outward from the shuttle 192. This ensures that, when the first tab 194 is moved distally toward the resection activating mechanism 161, the first tab 194 is urged radially outward to secure the first tab 194 between the cog teeth 167. Similarly, when the second tab 195 is moved proximally toward the gap adjust ring 141, the biasing spring 196 urges the second tab 195 radially outward to secure the second tab 195 between the cog teeth 143.

Figure 14:
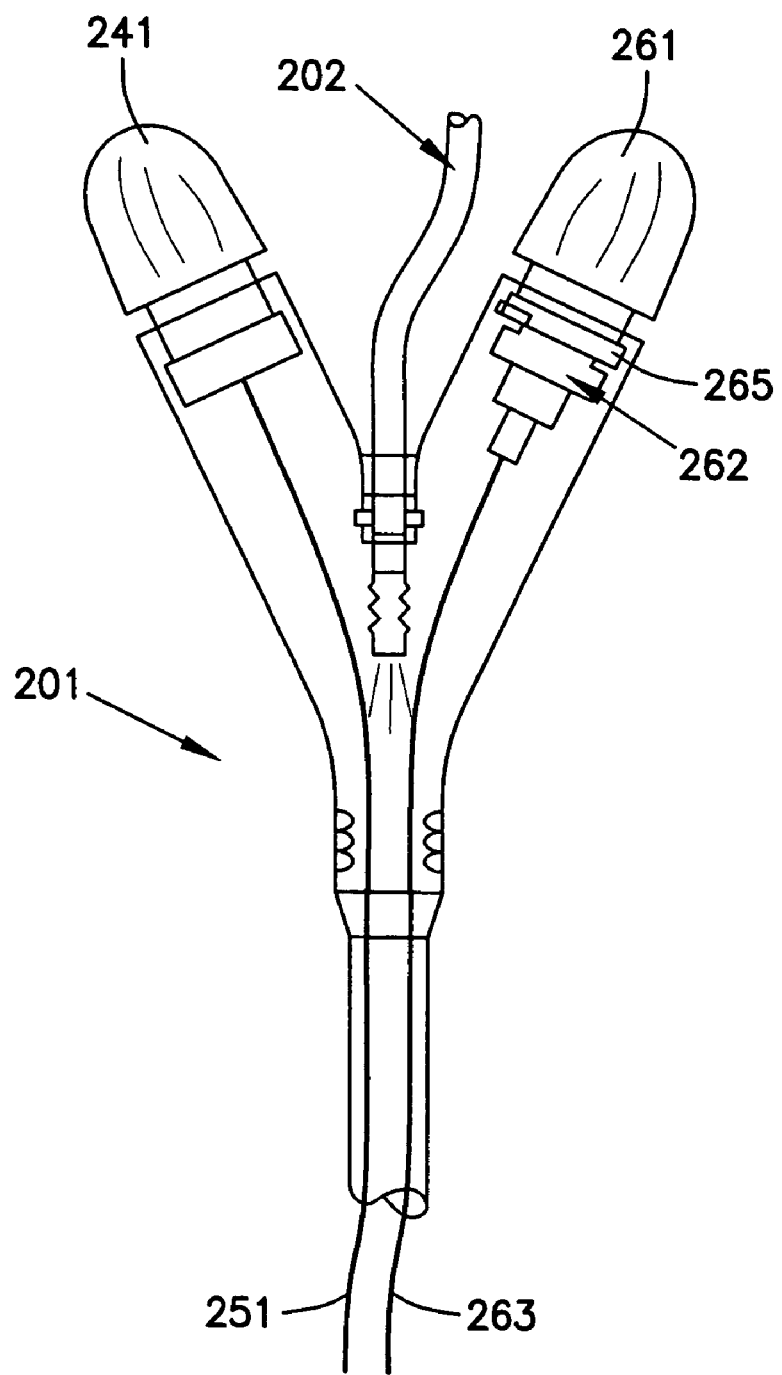
FIG. 14 is a cross-sectional view of a second embodiment of a full thickness resection device control handle in accordance with the present invention.
Figure 15:
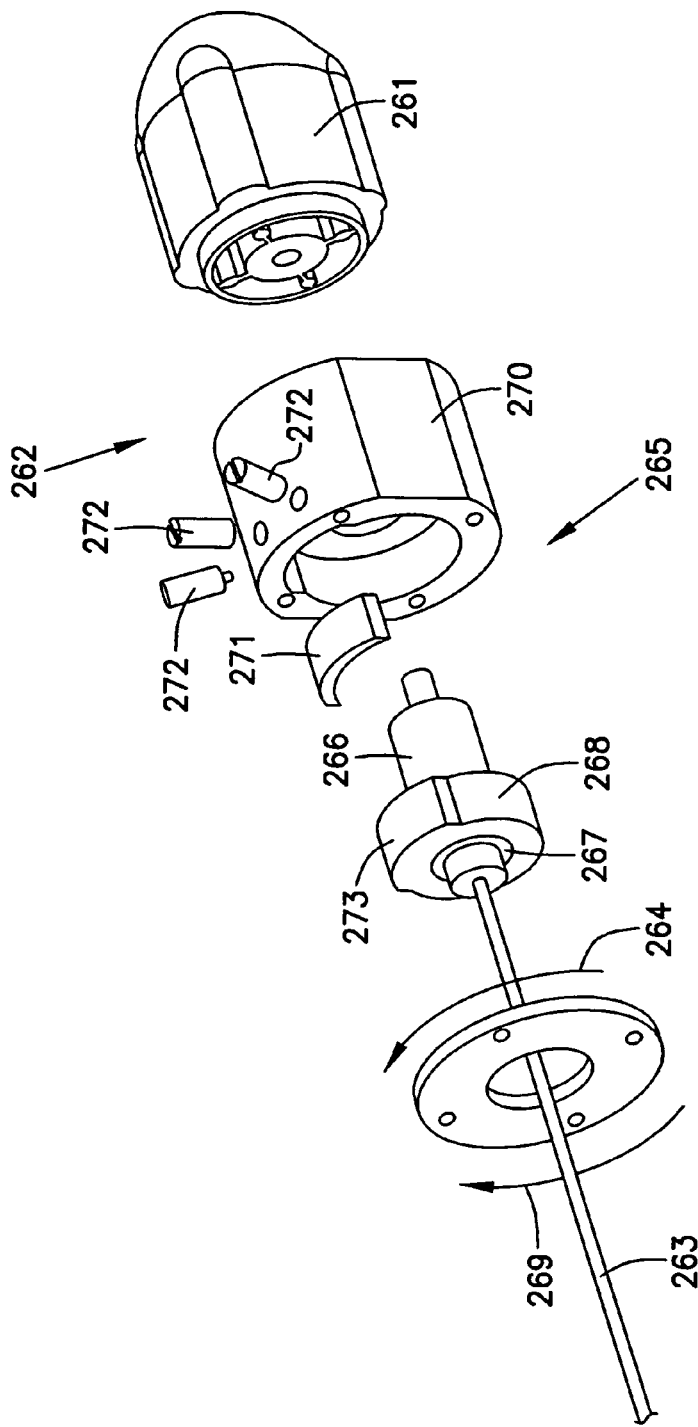
FIG. 15 is an exploded perspective view of a portion of the control handle of FIG. 14.
Figure 16:
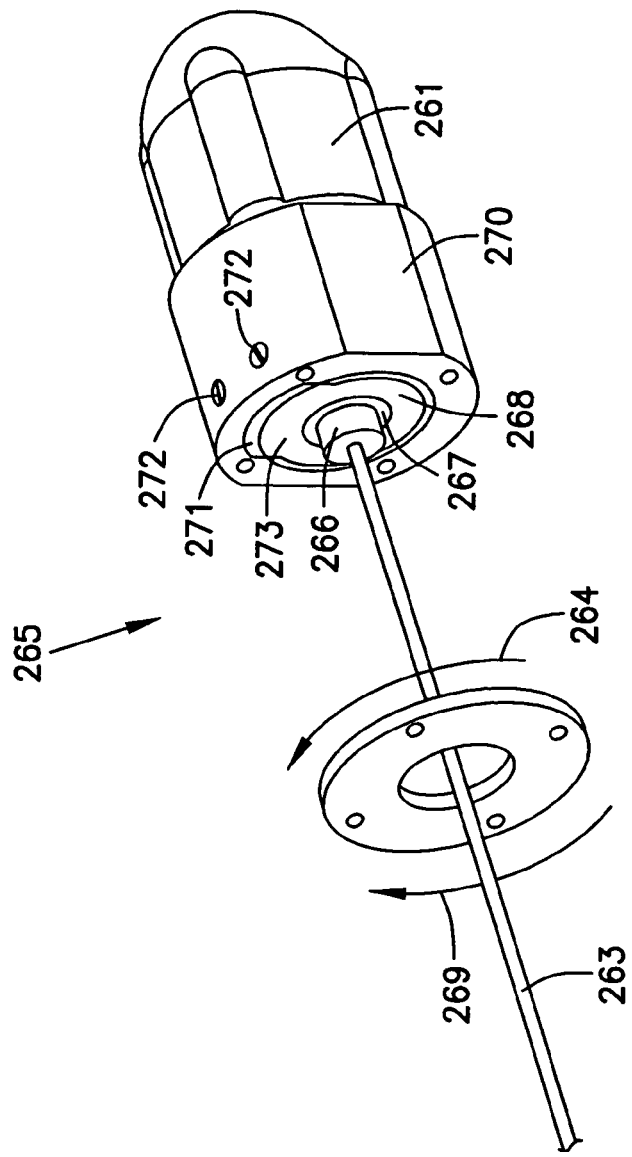
FIG. 16 is a partially exploded perspective view of the portion of the control handle of FIG. 14.

FIGS. 14 through 16 illustrate second embodiment of the present invention including an alternative controlling device 262 including a brake shoe assembly 265 which controls the release rate of torsional energy stored in a flexible drive shaft 263 during rotation in a first direction (e.g., during stapling). The brake shoe assembly 265 engages the flexible drive shaft 263 and functions with a staple-cut knob 261 in a first branch of a Y-shaped control handle 201. Alternatively, controlling device 262 may be configured to function inside a control handle 201 with a concentric staple-cut ring and gap adjust ring design, as described in regard to the first embodiment. A gap adjust ring 241 acts on a drive shaft 251 in the second branch of the control handle 201, through which an endoscope 202 may also be inserted.

As illustrated in more detail in FIGS. 15 and 16, the brake shoe assembly 265 includes a clutch 267, a stapling casing 270, a spring-loaded brake pad 271, and a hub 268 which may be formed as a disc surrounding and engaging the clutch 267. A rigid drive shaft 266 couples the staple firing ring 261 to the flexible drive shaft 263. A proximal end of the rigid drive shaft 266 is screwed into the staple firing ring 261 and a proximal end of the flexible drive shaft 263 is coupled to a distal end of the rigid drive shaft 266 (e.g., by being plugged into a mating opening in the distal end of the rigid drive shaft 266). The clutch 267 acts as a directional control mechanism, engaging and surrounding a portion of the rigid drive shaft 266 to permit rotation thereof inside the clutch 267 only in a first direction 264. Thus, the rigid drive shaft 266 and the flexible drive shaft 263 may rotate together freely inside the clutch 267 only in the first direction 264 to accomplish a first operative procedure, e.g., tissue stapling. As described above in regard to the first embodiment, rotation of the flexible drive shaft 263 in the first direction 264 may drive a stapling mechanism at the distal end of the device (not shown) to fire staples from the stapling head into the tissue. The clutch 267 is coupled to the other elements of the brake shoe assembly 265 as described below to prevents a user from beginning a second operative procedure, tissue cutting, before completing the first operative procedure, by preventing free rotation of the rigid drive shaft 266 and the flexible drive shaft 263 in a second direction 269 while the clutch 267 is engaged.

During the first operative procedure, rotation of flexible drive shaft 263 in the first direction 264 through the staple firing range results in a build up of torsional energy in the flexible drive shaft 263. As described above, the release of this torsional energy stored in the flexible drive shaft 263 is controlled during a second operative procedure (e.g., tissue cutting) by the engagement of the rigid drive shaft 266 and the clutch 267 in conjunction with the other components in the brake shoe assembly 265.

Flexible drive shaft 263, rigid drive shaft 266, clutch 267, and disk 268 all are moveably mounted within a stapling casing 270 so that they may rotate therein. A brake pad 271 is mounted on a portion of an inner surface of the stapling casing 270 with springs 272 biasing the brake pad 271 toward the disk 268. This causes the brake pad 271 to engage a pawl ring portion 273 of an outer edge of the disk 268 to provide frictional resistance to the movement of disk 268 as the pawl ring portion 273 comes into contact with the brake pad 271.

As described above, once the user has fully completed the first operative procedure, in order to begin the second operative procedure (e.g., tissue cutting), the user begins rotating the staple firing ring 261 in the second direction 269 to rotate the rigid drive shaft 266 and the flexible drive shaft 263 in the second direction 269. As discussed above, the clutch 267 prevents counterclockwise rotation of the rigid drive shaft 266 and the flexible drive shaft 263 therewithin. Thus, during rotation of the staple firing ring 261 in the second direction 269, the rigid drive shaft 266 engages the clutch 267 and the disk 268 driving rotation of the entire assemblage of the flexible drive shaft 263, the rigid drive shaft 266, the clutch 267 and the disk 268 also in second direction 269.

Initially, during rotation of the staple firing ring 261 in the second direction 269 to begin the second operative procedure, the pawl ring portion 273 is in contact with the brake pad 271, which, with the aid of the springs 272, exerts a resisting frictional force against the motion of the rigid drive shaft 266, the clutch 267, and the disk 268 for the length of the pawl ring portion 273 (otherwise known as the dwell period for the pawl ring portion 273). In order to rotate the rigid drive shaft 266 and the flexible drive shaft 263 in the second direction 269 to begin a cutting procedure, the user must apply enough force to overcome the frictional resistance exerted by brake pad 271 on disk 268. This frictional resistance also resists rotation in the second direction 269 through release of the torsional energy stored in the flexible drive shaft 263 during the first operative procedure.

As will be understood by those of skill in the art, the length of the pawl ring portion 273 may be determined as a function of an amount of torsional energy stored in the flexible drive shaft 263 during staple firing procedures, so that the torsional energy stored therein is completely dissipated before the dwell period for the pawl ring portion 273 has expired. In this embodiment, rotation of staple firing ring 261 will not drive the flexible drive shaft 263 to begin the cutting procedure until the torsional energy has been released at a controlled rate while pawl ring portion 273 of disk 268 is in contact with brake pad 271. Once the pawl ring portion 273 is no longer in contact with the brake pad 271 and all of the stored torsional energy has been released, continued rotation of the staple firing ring 261 in the second direction 269 to complete the cutting procedure is driven solely by force applied by the user to the staple firing ring 261. At this point, the force applied by the user drives the rigid drive shaft 266 and the flexible drive shaft 263 freely to actuate a cutting mechanism (not shown) coupled to a distal end of the flexible drive shaft 263.

At the end of the cutting procedure, the flexible drive shaft 263 will store torsional energy biasing the flexible drive shaft to rotate in the first direction 264. However, this stored torsional energy is not sufficient to actuate a stapling mechanism to begin firing staples in an uncontrolled manner, due to the increased higher level of energy required for the stapling operation than is required to drive a cutting mechanism.

Figure 17:
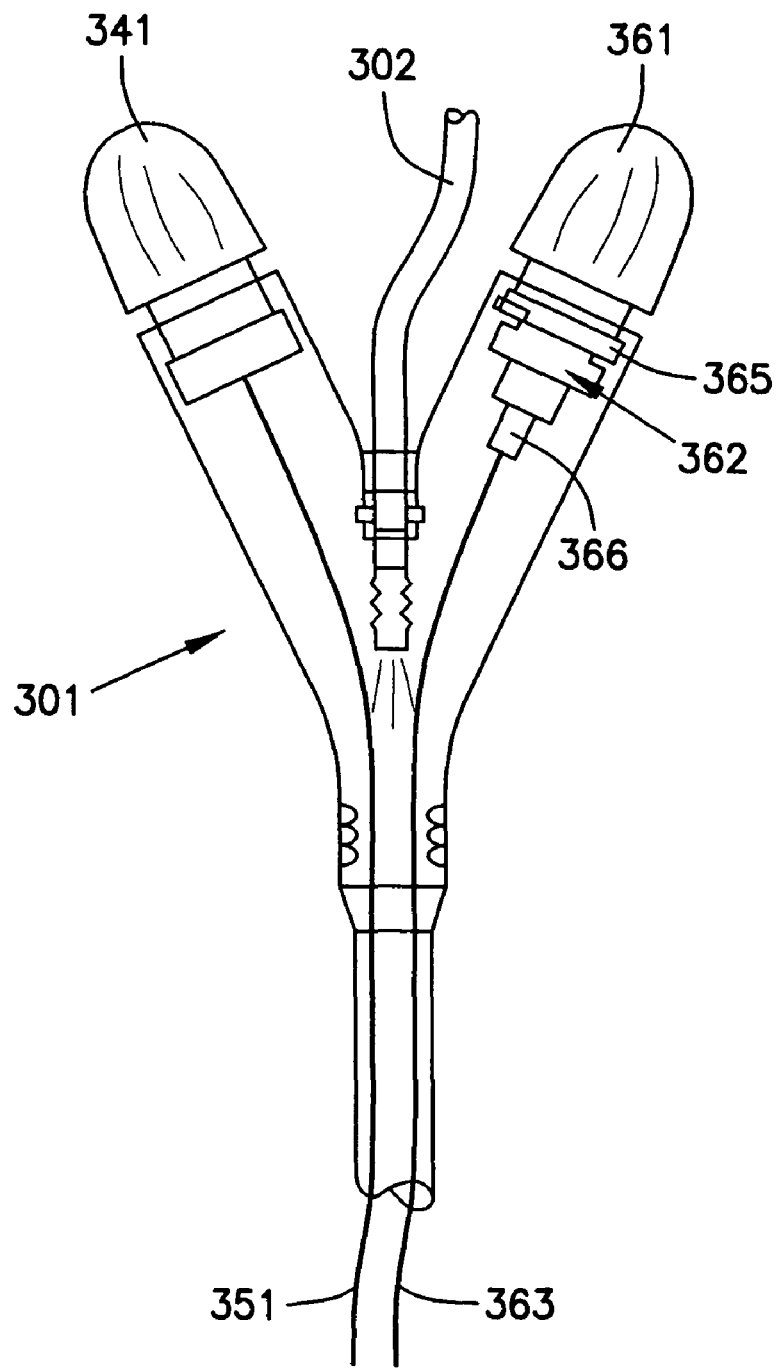
FIG. 17 is a cross sectional view of a third embodiment of a full thickness resection device control handle in accordance with the present invention.
Figure 18:
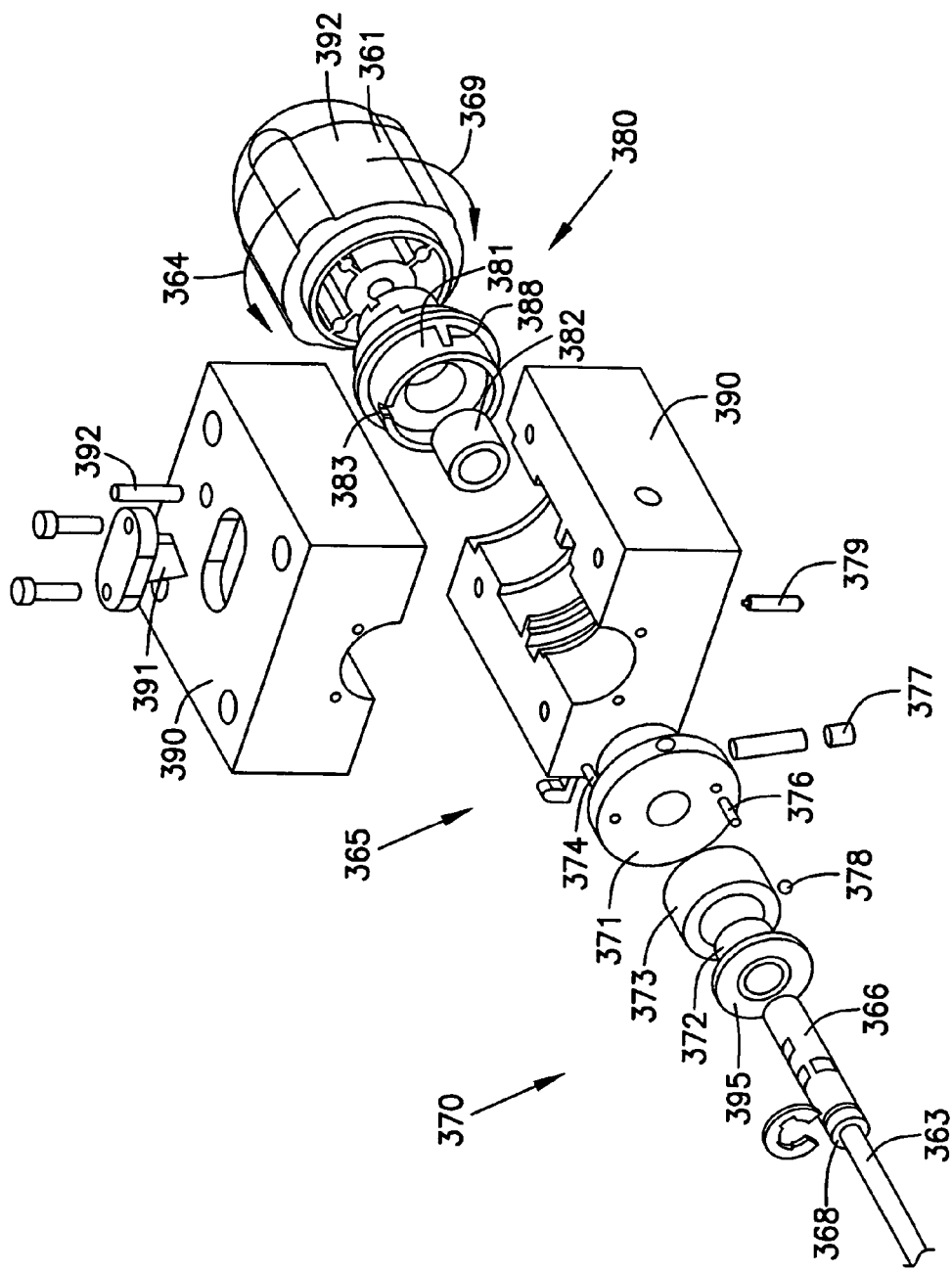
FIG. 18 is an exploded perspective view of a portion of the control handle of FIG. 17.
Figure 19:
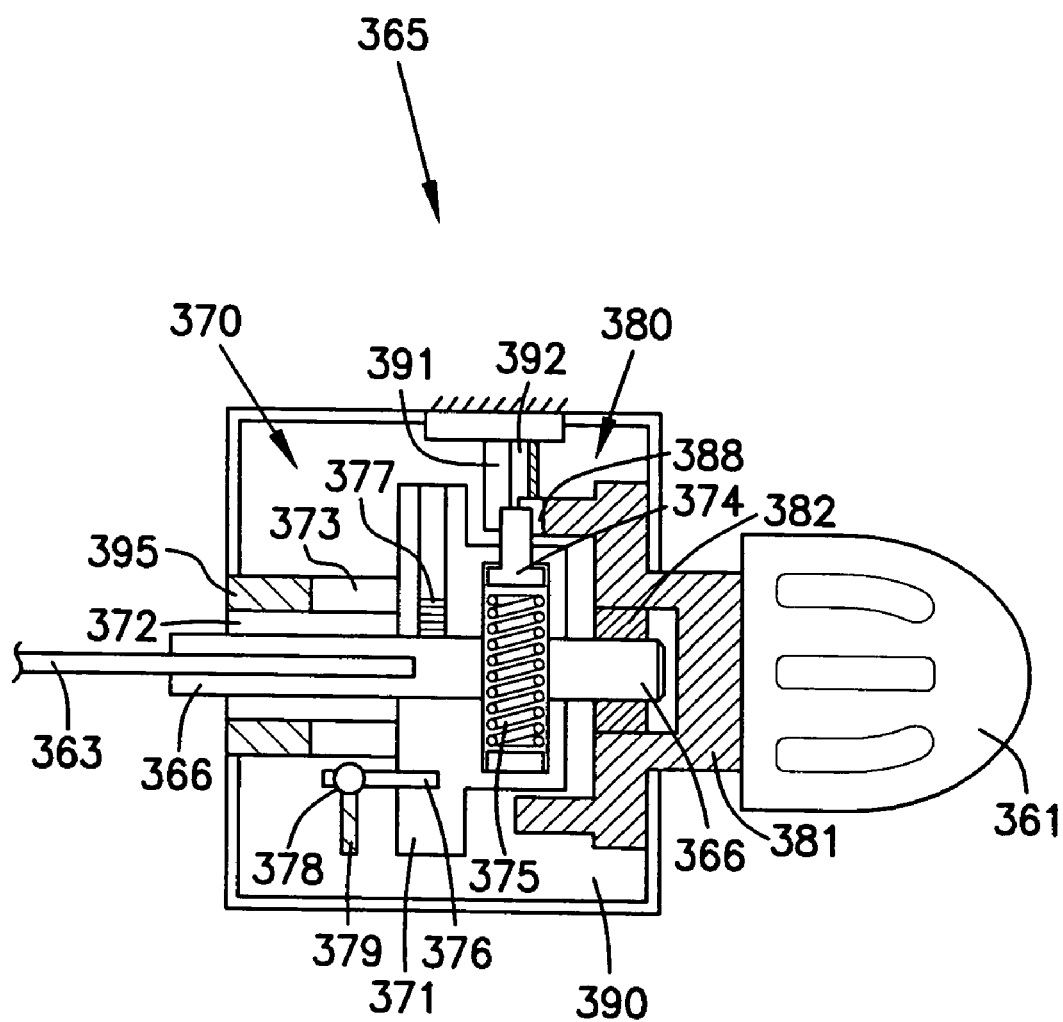
FIG. 19 is a cross-sectional view of a portion of the control handle of FIG. 18.

In a third embodiment of the present invention shown in FIGS. 17 through 19, a double clutch assembly 365 operates as another configuration of a controlling device 362 which controls a release rate, during a second operative procedure, of torsional energy stored in a flexible drive shaft 363 during the driving of the flexible drive shaft 363 in a first operative procedure. The double clutch assembly 365, as explained below, serves not only to control the dissipation of torsional energy built up in the flexible drive shaft 363 during rotation in a first direction but also serves as a type of staple-cutting lockout mechanism preventing a user from beginning a second operative procedure before completing the first operative procedure.

As shown in FIG. 17, the double clutch assembly 365 functions with a staple-cut knob 361 and the flexible drive shaft 363 in one branch of a Y-shaped control handle 301, while a gap adjustment knob acts on a drive shaft 351 in the other branch of the control handle 301. As shown in FIGS. 18 and 19, the double clutch assembly 365 includes two rotational assemblies, 370, 380, an assembly housing 390, a decoupling cam 391, a stop cam 392, and a washer 395. The decoupling cam 391 and the stop cam 392 are attached to the assembly housing 390 and act upon rotational assemblies 370, 380 as explained further below. The washer 395 surrounds rigid drive shaft 366 at a distal side of the assembly housing 390 and rotates with the rigid drive shaft 366 rubbing against an interior surface of the assembly housing 390 to control a rate of rotation of the rigid drive shaft 366, as further explained below.

The rotational assembly 370 includes a lockhousing 371, a roller clutch 372, a pawl ring 373, a set screw 377, a ball bearing 378, and a plunge spring 379. The set screw 377 secures the lockhousing 371 to the rigid drive shaft 366 so that the lockhousing 371 rotates with the rigid drive shaft 366. The rigid drive shaft 366 is not attached to the staple-cut knob 361. However, rotation of the rigid drive shaft 366 is indirectly driven by rotation of the staple-cut knob 361 through interaction of the components in the double clutch assembly 365 as explained further below. The roller clutch 372, resting inside the pawl ring 373, engages and surrounds the rigid drive shaft 366 to permit rotation thereof inside the clutch 372 only in a first direction 364, for example clockwise, during a tissue stapling procedure.

The rotational assembly 380 includes a lockplate 381 and a roller clutch 382. The lockplate 381 is coupled to the staple-cut knob 361 so that the lockplate 381 rotates with the staple-cut knob 361. The roller clutch 382 rests inside the lockplate 381, engaging and surrounding a first portion of the rigid drive shaft 366 and only permits the rigid drive shaft 366 to rotate inside the clutch 382 in a second direction 369 opposite to the first direction 364. In this example, if clutch 372 permits rigid drive shaft 366 to rotate freely in first direction 364, then clutch 382 permits rigid drive shaft 366 to rotate freely in second direction 369.

In the rotational assembly 370, the lockhousing 371 includes a coupling pin 374, a spring 375 and a decoupling pin 376. The coupling pin 374 is biased outward by a spring 375 to engage a notch 383 in the lock plate 381 to couple the lockhousing 371 to the lockplate 381. Rotation of the staple-cut knob 361 in the first direction 364 drives rotation of the lockplate 381 and the lockhousing 371 in the first direction 364 which, in turn, drives rotation of the rigid drive shaft 366 and the flexible drive shaft 363 inside the clutch 372 also in the first direction 364 to drive a stapling mechanism, as described above. When this rotation is occurring, the pawl ring 373 and the clutch 372 do not rotate relative to the assembly housing 390 as a flat surface of the pawl ring 373 engages ball bearing 378 mounted in assembly housing 390. The ball bearing 378 prevents the pawl ring 373 and the clutch 372 from rotating inside the assembly housing 390. The ball bearing 378 is biased against the pawl ring 373 by a plunge spring 379. Upon further rotation of the lockhousing 371 to a point at which a stapling operation has been completed, the decoupling pin 376 comes into contact with the ball bearing 378 and moves the ball bearing 378 further into assembly housing 390 against bias of plunge spring 379 out of position. This then allows the pawl ring 373 and the clutch 372 to rotate relative to the assembly housing 390.

As long as the pawl ring 373 and the clutch 372 are coupled to the assembly housing 390 and the lockhousing 371 is coupled to the lockplate 381, the clutch 372 prevents a user from rotating the staple-cut knob 361 in the second direction 369 to drive rotation of the rigid drive shaft 366 and the flexible drive shaft 363 in the second direction 369. As explained further below, the pawl ring 373 and the clutch 372 are not decoupled from the assembly housing 390 and the lockhousing 371 cannot be decoupled from lockplate 381 until the user has rotated the staple-cut knob in the first direction 364 sufficiently to complete a tissue stapling procedure. Thus, the two couplings and the restricted one-way rotation permitted inside the clutch 372, together function as a safety staple-cutting lockout mechanism preventing a user from beginning a second operative procedure, until the user has completed rotation of the staple-cut knob 361 and the flexible drive shaft 363 in first direction 364 to complete the first operative procedure.

When the user has reached the end of the tissue stapling procedure, further rotation of the staple-cut knob 361 in the first direction 364 along with the lockhousing 371 and the lockplate 381, first brings the decoupling pin 376 into contact with the ball bearing 378, thereby decoupling the pawl ring 373 and the clutch 372 from the assembly housing 390. After the ball bearing 378 has moved out of position, the pawl ring 373 and the clutch 372 may rotate freely in either direction 364 or 369, along with the rigid drive shaft 366 and the flexible drive shaft 363.

After the pawl ring 373 and the clutch 372 have been decoupled from the assembly housing 390, further rotation of the staple-cut knob 361 in the first direction 364 decouples the lockhousing 371 from the lockplate 381. This rotation of the staple-cut knob 361 in the first direction 364 brings the coupling pin 374 on the lockhousing 371 into contact with the decoupling cam 391. The decoupling cam 391 depresses the coupling pin 374 inward against the biased spring 375 as the lockhousing 371 is rotated in the first direction 364 through rotation of the staple-cut knob 361 and the lockplate 381 in the first direction 364. Once the coupling pin 374 has been sufficiently depressed inward to disengage from the notch 383, the lockhousing 371 is decoupled from the lockplate 381, and rotation of the staple-cut knob 361 and the lockplate 381 in the first direction 364 no longer drives rotation of the lockhousing 371, the rigid drive shaft 366 and the flexible drive shaft 363.

Once both decouplings have occurred, further rotation of the staple-cut knob in the first direction 364 does not drive further rotation of the lockhousing 371 and the rigid drive shaft 366 and the flexible drive shaft 363. The flexible drive shaft 363 releases torsional energy stored during rotation in the first direction 364 during the tissue stapling procedure, by unwinding in the second direction 369, thereby rotating the rigid drive shaft 366 along with lockhousing 371, the clutch 372 and the pawl ring 373 in the second direction 369 inside the clutch 382. Since the clutch 382 permits the rigid drive shaft 366 to rotate freely inside the clutch 382, rotation of the rigid drive shaft 366 in the second direction 369 does not engage the clutch 382, the lockplate 381 or the staple-cut knob 361.

The washer 395 surrounding the rigid drive shaft at a distal side of the assembly housing 390 and rotating with the rigid drive shaft 366, rubs against the assembly housing 390 to slow the rotation rate of the rigid drive shaft 366. Friction created by the washer 395 between the rigid drive shaft 366 and the assembly housing 390 prevents the flexible drive shaft 363 from rotating in the second direction 369 during the course of its unwinding. Thus, both decouplings and the washer 395 together function as part of the controlling device 362 to control a dissipation of the stored torsional energy.

After both decouplings have occurred, further rotation of the staple-cut knob 361 (no longer driving rotation of the lockhousing 371, the rigid drive shaft 366 and the flexible drive shaft 363) in the first direction 364 brings the stop pin 388 on the lockplate 381 into contact with the stop cam 392 inside the assembly housing 390 and prevents the staple-cut knob 361 and the lockplate 381 from rotating further in the first direction 364. Those skilled in the art will understand that the positions of the coupling pin 374 and the decoupling pin 376 on the lockhousing 371 and the position of the stop pin 388 on the lockplate 381 are selected so that, after the rotating the staple-cut knob 361 in the first direction 364 through an arc long enough to completely fire the complete range of staples from the stapling head in the distal end of the full thickness resection device into the tissue, the user is prevented from further rotating the staple-cut knob in the first direction. Thus, when the staple-cut knob 361 can no longer be rotated in the first direction 364, the user knows that the device has completed the tissue stapling procedure and the user may begin the tissue cutting procedure by rotating staple-cut knob 361 in the second direction 369 to drive rotation of the flexible drive shaft 363 and actuate a cutting mechanism.

Rotation of the staple-cut knob 361 in the second direction 369 rotates the lockplate 381 and the roller clutch 382 also in the second direction 369. Although the roller clutch 382 permits the rigid drive shaft 366 to rotate freely inside the roller clutch 382 in the second direction 369, rotation of the roller clutch 382 in the second direction 369 engages and drives the rigid drive shaft 366 (along with the lockhousing 371, the pawl ring 373 and the clutch 372) to rotate in the second direction 369 inside the assembly housing 390. Rotation of the rigid drive shaft 366 in the second direction 369 rotates the flexible drive shaft 363 in the second direction 369. Thus, a user rotating the staple-cut knob 361 in the second direction 369 rotates the lockplate 381, the roller clutch 382, the rigid shaft 366 and the flexible drive shaft 363 to engage the cutting mechanism.

Figure 20:
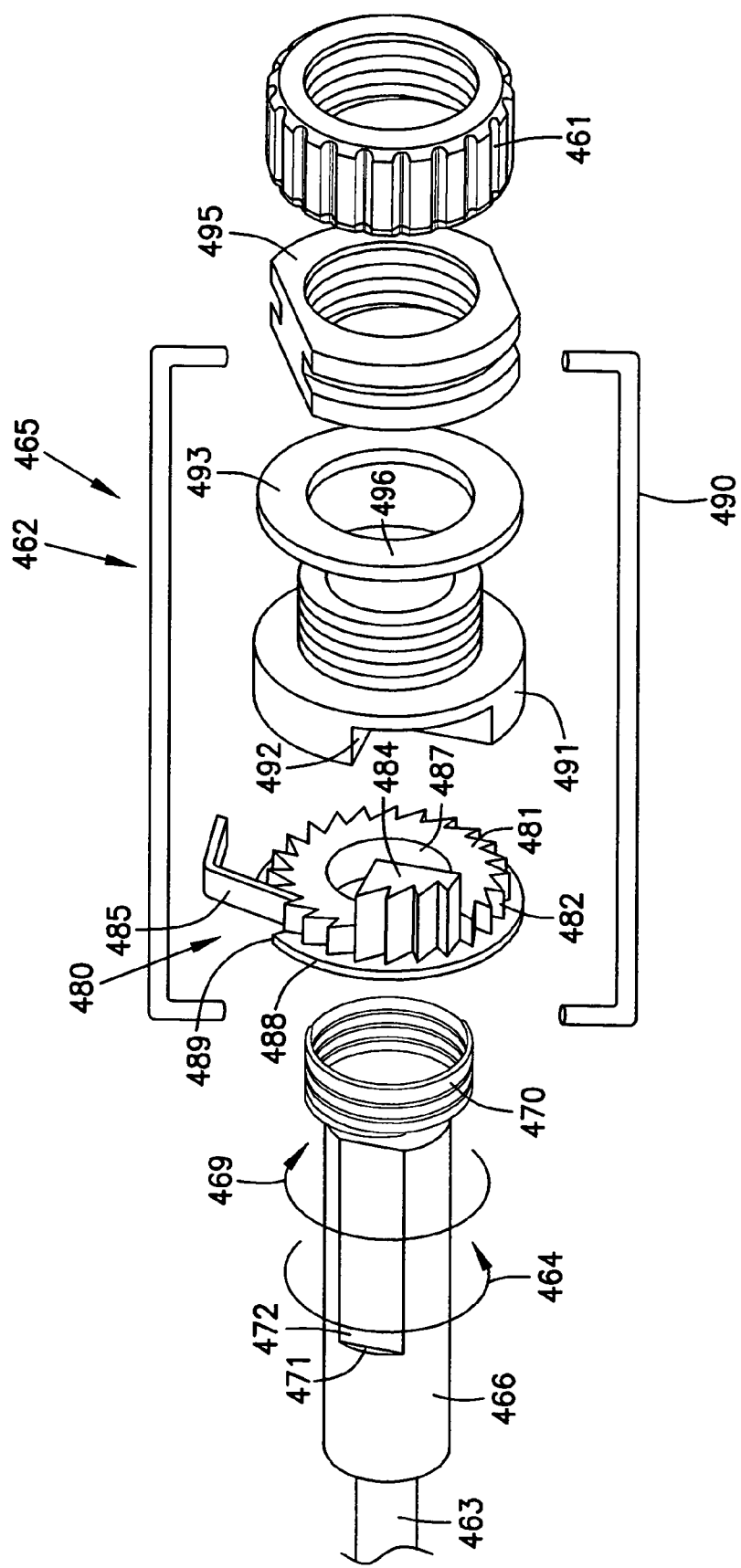
FIG. 20 is an exploded perspective view of a portion of a fourth embodiment of a full thickness resection device control handle in accordance with the present invention.
Figure 21:
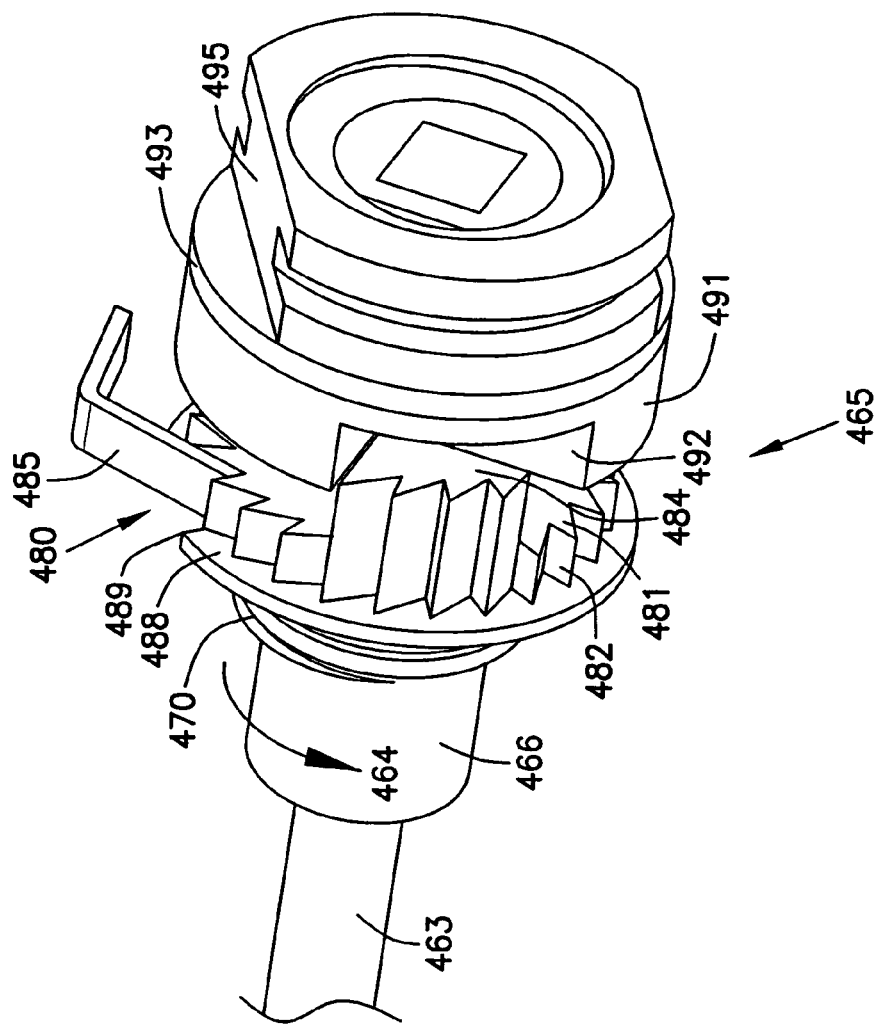
FIG. 21 is a perspective view of the portion of the control handle of FIG. 20.

A fourth embodiment of the present invention depicted in FIGS. 20 and 21 presents an alternative controlling device 462 including a torsion balancing assembly 465 engaging a rigid drive shaft 466 and a flexible drive shaft 463 to control, during a second operative procedure, the release rate of torsional energy stored in flexible drive shaft 463 during a first operative procedure. The torsion balancing assembly 465, as explained below, serves not only to control the dissipation of torsional energy stored in the flexible drive shaft 463 but also acts as a staple-cutting lockout mechanism, to prevent a user from beginning a second operative procedure before completing a first operative procedure.

As described in regard to the previous embodiments, the torsion balancing assembly 465 may function either with a staple-cut knob 461 mounted in either a Y-shaped control handle or in a control handle with concentric staple-cut and gap adjust rings. Furthermore, those skilled in the art will understand that a wide variety of control handle shapes and configurations may be employed with the apparatus according to the present invention. In the illustrations of this fourth embodiment in FIGS. 20 and 21, rotation of a flexible drive shaft 463 in a first direction 464 engages a stapling mechanism at a distal end of a full thickness resection device. As shown in FIG. 20, the first and second directions 464, 469, respectively, in this embodiment are opposite the first and second directions employed in the previous embodiments. Rigid drive shaft 466 runs through the entire torsion balancing assembly 465 and is screwed into a staple-cut knob 461 at a proximal end of the rigid drive shaft 466. A proximal end of the flexible drive shaft 463 is coupled to a distal end of the rigid drive shaft 466.

The torsion balancing assembly 465 includes a spring 470, a ratchet assembly 480, a housing 490, a bolt 491, a bellville washer 493 and a nut 495. The nut 495 is secured to the housing 490 and does not rotate relative to the staple-cut knob 461. The bolt 491 is screwed into the nut 495, with the bellville washer 493 between the bolt 491 and the nut 495.

During initial assembly of the torsion balancing assembly 465, when the bolt 491 is screwed into the nut 495, sufficient torque is used so that, once assembled, the bolt 491, the bellville washer 493 and the nut 495 together store a predetermined amount of torsional energy therein substantially equal to and opposite an amount of torsional energy stored in the assembly during rotation of the rigid drive shaft 466, the staple-cut knob 461 and the flexible drive shaft 463 in the first direction 464 during a stapling operation. The predetermined amount of torsional energy stored in the assembled bolt 491, bellville washer 493 and nut 495 may be substantially equal to or a predetermined amount less than an amount of torsional energy stored in the flexible drive shaft 463 during rotation in the first direction 464 in a tissue stapling procedure. As further explained below, the torsional energy stored in the assembled bolt 491, bellville washer 493 and nut 495 is oriented opposite the torsional energy stored in the flexible drive shaft 463 during rotation in the first direction 464 in a tissue stapling procedure so that these oppositely oriented torsional energies cancel a portion or all of one another out. Thus, as a user begins to rotate the staple-cut knob in the second direction after completing the stapling operation, the torsion balancing assembly 465 has dissipated a portion or all of the torsional energy stored in flexible drive shaft 463 during the stapling operation.

A ratchet assembly 480 includes a ratchet 481, a pawl 485 and a ratchet plate 488. The ratchet 481 is attached to the ratchet plate 488, and both are moveably mounted inside the housing 490. A surface 472 on the rigid drive shaft and a flat portion (not shown) of an inside surface 487 of the ratchet 481 couples the ratchet 481 to the drive shaft 466, so that the ratchet 481 and the ratchet plate 488 rotate with the rigid drive shaft 466 in either the first or second direction 464, 469, respectively. The ratchet 481 includes teeth 482 around all or a portion thereof The pawl 485 is coupled to the housing 490 and is engageable with the teeth 482 on the ratchet 481 to prevent the rigid drive shaft 466 and the staple-cut knob 461 rotating in the second direction 469 until the stapling operation has been completed.

As the staple-cut knob is rotated by a user in the first direction 464, the rigid drive shaft 466, the flexible drive shaft 463 and the ratchet 481 are rotated in the first direction 464 relative to the bolt 491, washer 493 and nut 495 through the full firing range of the stapling device. The pawl 485 engages with the teeth 482 to prevent the ratchet 481, the rigid drive shaft 466 and the flexible drive shaft 463 from rotating in the second direction 469 even if the user applies force in this direction to the staple-cut knob 461. Thus, the ratchet is designed so that the teeth 482 thereof extend around an arc corresponding to the fill firing range of the stapling mechanism. Throughout this range, the pawl 485 prevents the ratchet 481 from rotating in the second direction 469. Consequently, the rigid drive shaft 466 and the flexible drive shaft 463 are also prevented from rotating in the second direction 469 and operating a tissue cutting mechanism until the stapling operation has been completed. The bolt 491 is not coupled to the rigid drive shaft 466 until the rotation of the flexible drive shaft 463 and the rigid drive shaft 466 in first direction 464 has been completed.

Once the staple firing procedure has been completed, the pawl 485 is disengaged from the teeth 482 of the ratchet 481 by passing through the cutout portion 484 formed on the ratchet 481, catch notch 492 on bolt 491, open notch portion 489 on ratchet plate 488 and spring 470, as explained further below. Once the pawl 485 has been disengaged, the staple-cut knob 461, the rigid drive shaft 466 and the flexible drive shaft 463 may rotate in the second direction 469 to commence the tissue cutting procedure.

At the end of staple firing procedure, rotation in the first direction 464 of the staple-cut knob 461 along with the rigid drive shaft 466 and the flexible drive shaft 463 brings the cutout portion 484 of the ratchet 481 and the open notch portion 489 of the ratchet plate 488 into alignment with the catch notch 492 in the bolt 491 as, at this stage, the bolt 491 is not yet coupled to or rotating with the rigid drive shaft 466. The spring 470 which is held in place by edge 471 at the distal end of the surface 472 of the rigid drive shaft 466, biases the ratchet plate 488 and the ratchet 481 toward the bolt 491 to couple the ratchet 481 to the bolt 491 when the cutout portion 484 becomes aligned with the catch notch 492 (i.e., the cutout portion 484 of the ratchet 481 is moved proximally into the catch notch 492 in the bolt 491). The pawl 485 which is coupled to the housing 490 and remains stationary relative to the proximal movement of the ratchet plate 488 and the ratchet 481, disengages from the teeth 482 during this coupling. Disengagement occurs because, as the ratchet plate 488 and the ratchet 481 move proximally toward the bolt 491, the open notch portion 489 of the ratchet plate 488 permits the ratchet plate 488 and the ratchet 481 to clear the pawl 485.

Once the pawl 485 has been disengaged from the ratchet 481, and the ratchet 481 has been coupled to the bolt 491, the ratchet plate 488, the ratchet 481 and the bolt 491 may all rotate together with the rigid drive shaft 466 within the housing 490. Further rotation of the staple-cut knob 461 in the first direction 464 may be prevented, for example, by a stop pin on ratchet 481 which may be brought into contact with a stop cam attached to housing 490. Alternatively, as shown in this embodiment, if the bolt 491 is screwed into the nut 495 during the initial assembly of the torsion balance assembly 465, the staple-cut knob 461 is blocked from further rotation in the first direction 464 once the ratchet 481 has been coupled to the bolt 491. After the bolt 491 has been coupled to the ratchet 481, attempts to further rotate the staple-cut knob 461 in the first direction 464 rotate the coupled ratchet 481 and the bolt 491 which simply operates to screw the bolt 491 further onto the nut 495. The nut 495 which is secured to the assembly housing 490, is stationary relative to the movement of the bolt 491 and prevents any further rotation of bolt 491. Consequently, further rotation of the ratchet 481, the rigid drive shaft 466, the flexible drive shaft 463 and the staple-cut knob 461 in the first direction 464 is prevented.

Those skilled in the art will understand that the positions of the cutout portion 484, the notch portion 489, and the catch notch 492 should preferably be configured so that, when the point is reached at which a user may no longer rotate the staple-cut knob 461 in the first direction 464, the flexible drive shaft 463 has rotated in the first direction 464 through an arc sufficient to completely fire the complete range of staples. Thus, when staple-cut knob 461 may no longer be rotated in the first direction 464, the user knows that the device has completed the tissue stapling procedure and the user may begin the tissue cutting procedure by rotating the staple-cut knob 461 in the second direction 469.

Then, when the user rotates the staple-cut knob 461 in the second direction 469, the ratchet plate 488, the ratchet 481 and the bolt 491 all rotate together in the second direction 469, driven by rotation of the rigid drive shaft 466 in the second direction 469. After an initial amount of rotation of the staple-cut knob 461 and the rigid drive shaft 466 in the second direction 469 has dissipated any torsional energy stored in the flexible drive shaft 463 not canceled by the torsion balancing assembly 465, further rotation of the staple-cut knob 461, the rigid drive shaft 466 and the flexible drive shaft 463 actuate the tissue cutting mechanism under control of the user.

A user's initial rotation of the staple-cut knob 461 and the rigid drive shaft 466 in the second direction 469, rotate the ratchet 481 and the bolt 491 in the second direction 469, loosening the bolt 491 and the bellville washer 492 from the nut 495 as the nut 495 is fixed to housing 490. Once the bolt 491 has been loosened, the torsional energy stored in the flexible drive shaft 463 is dissipated by acting on the bolt 491 to release the predetermined amount of torsional energy previously stored therein.

The amount of stored pre-determined torsional energy stored in the assembly of the bolt 491, the washer 493 and the nut 495 to effectively dissipate the torsional energy stored in the flexible drive shaft 463, as described above, may be adjusted by shaping the bellville washer 495 prior to the initial assembly of the torsion balance assembly 465 to provide a spring-like force or bias between the bolt 491 and the nut 495. In this embodiment, the bellville washer 493, does not rest flat on the surface of either the bolt 491 or the nut 495, but is warped or bent in a middle portion 496 thereof, although those skilled in the art will understand that any variety of shapes of bellville washers 493 may be employed to create the desired spring-like force between the bolt 491 and the nut 495 when assembled. The warped or bent shape of the bellville washer 493 gives the washer 493 a spring constant and deflection range engineered to dissipate the desired amount of torsional energy.

The amount of torsional energy stored in the assembly of the bolt 491, the washer 493 and the nut 495 may be pre-determined to be equal or substantially equal to the sum of the amount of torsional energy exerted by a user in the initial rotation of staple-cut knob in second direction (clockwise) to loosen bolt 491 and washer 493 from nut 495 in addition to an amount of torsional energy stored in the flexible drive shaft 463 during the stapling operation. For example, if it is estimated that the flexible drive shaft 463 stores 10 in.lb. of torque during the stapling operation, and that it takes 2 in. lb. of torque to loosen the bolt 491 from the nut 495 to begin rotation of the staple-cut knob 461 in the second direction 469, the amount of torque stored in the assembly of the bolt 491, the washer 493 and the nut 495 may preferably be adjusted to be at least 12 in. lb, if it is desired to have the entire 10 in. lb. of torque in the flexible drive shaft 463 dissipated at the start of the rotation of the staple-cut knob 461 in the second direction 469.

Once this torsional energy has been dissipated, further rotation by the user of the staple-cut knob 461, the rigid drive shaft 466 and the flexible drive shaft 463 in the second direction, unscrews or unwinds the bolt 491 from the nut 495 and the flexible drive shaft 463 engages the tissue cutting mechanism to begin the tissue cutting procedure.

As discussed above, there are a variety of configurations of locking mechanisms 190 available to alternatively the lock gap adjust assembly 140 and the resectioning assembly 160 against further rotation, so that, at any given time, a user may activate only one of these assemblies and perform only one of these procedures at any particular time.

Figure 22:
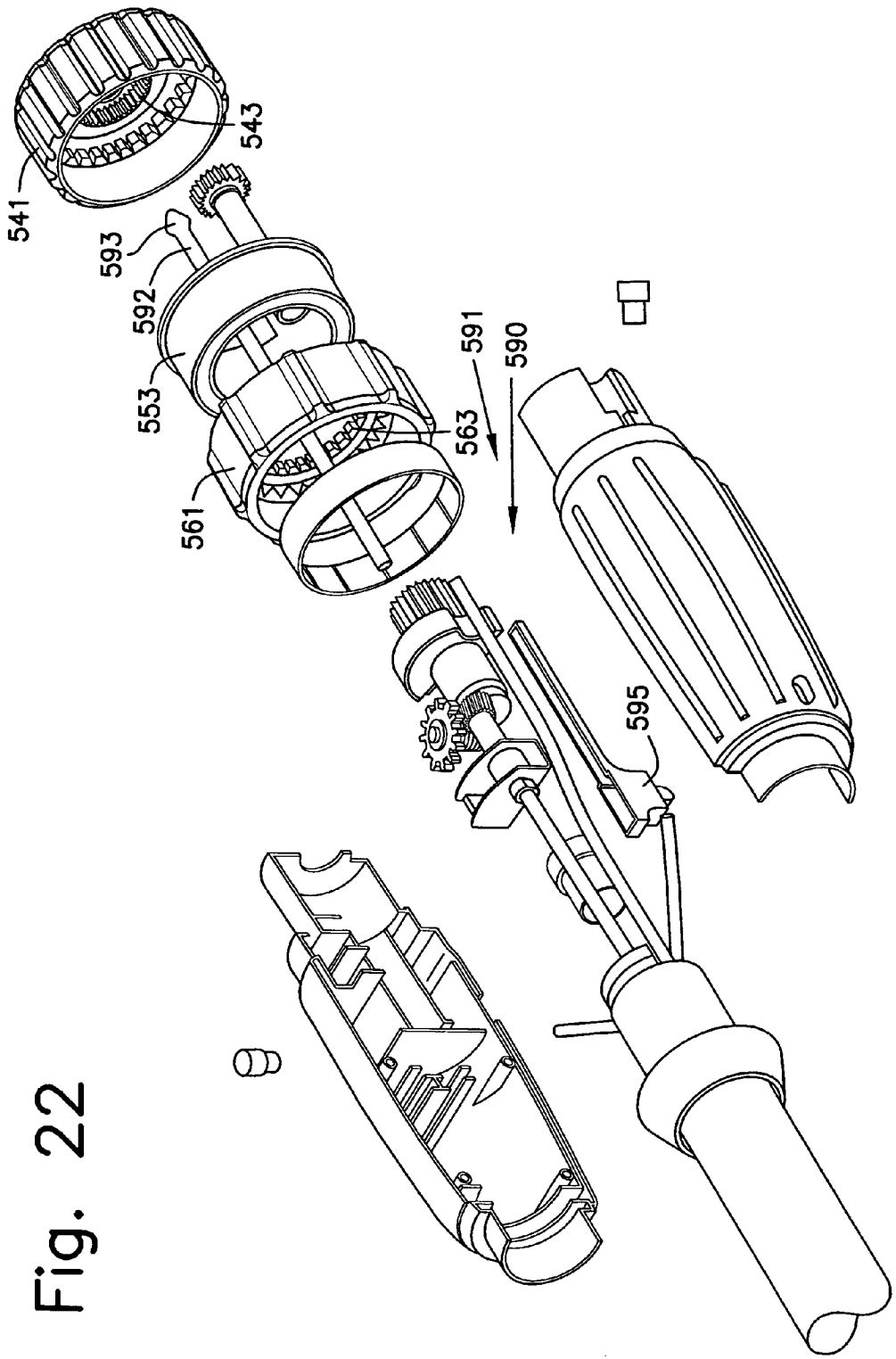
FIG. 22 is an exploded perspective view of a fifth embodiment of a full thickness resection device control handle in accordance with the present invention.
Figure 23:
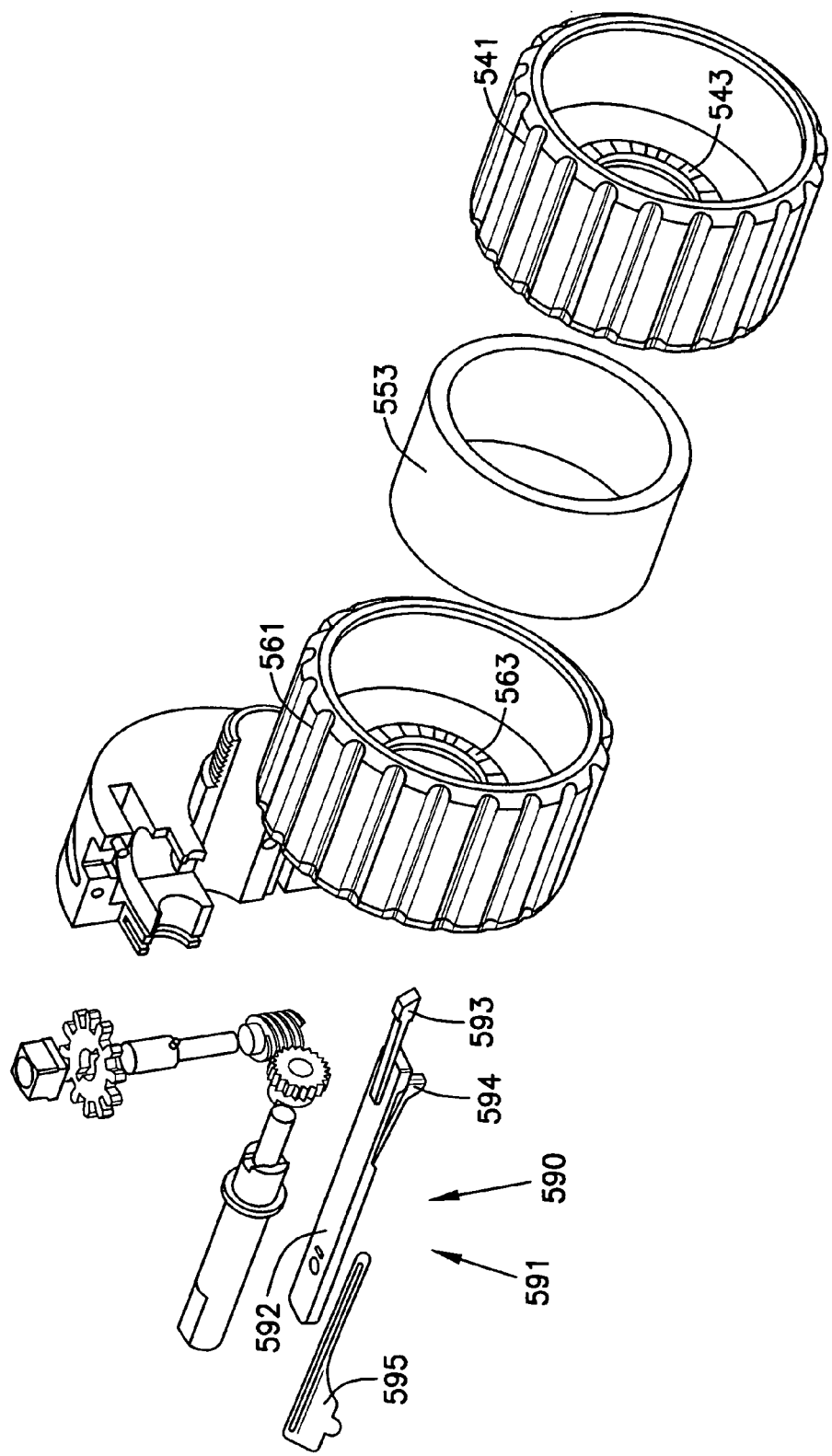
FIG. 23 is an exploded perspective view of a portion of the control handle of FIG. 22.
Figure 24:
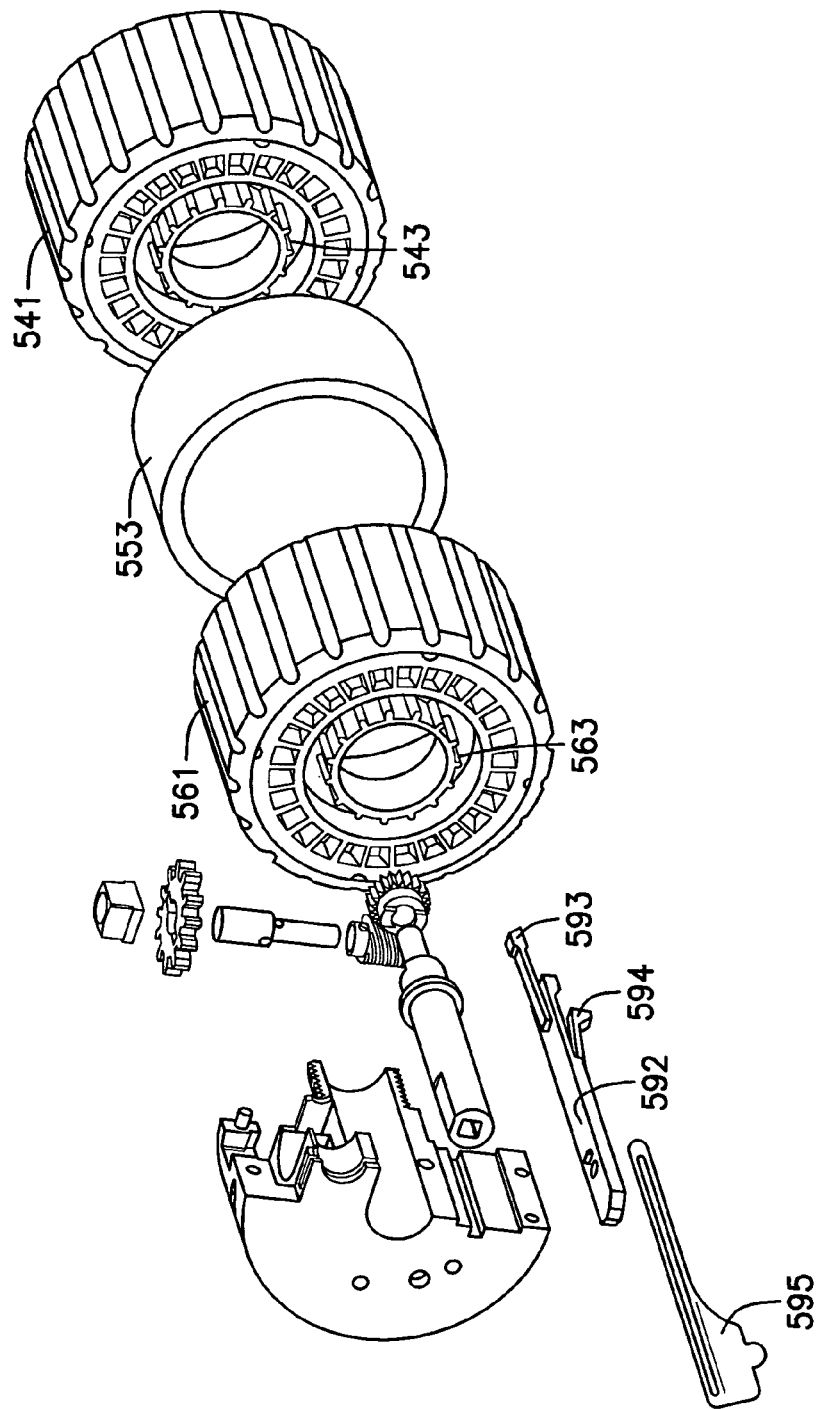
FIG. 24 is an exploded perspective view of the portion of the control handle of FIG. 23.

In a fifth embodiment of the present invention shown in FIGS. 22 through 24, a locking assembly 590 includes a lockout beam arrangement 591. The lockout beam arrangement 591 includes a lockout beam 592 and a switch beam 595. The lockout beam 592, which may, for example be formed as a cantilevered beam, is slidably disposed within a transition piece 553. A top portion of the lockout beam 592 is disposed within the switch beam 595 which may be utilized to slidably move the lockout beam 592 within the transition piece 553 so that the lockout beam 595 engages one of a gap adjust ring 541 and a staple firing ring 561. The lockout beam 592 includes a gap adjust lockout pawl 593 and a staple lockout pawl 594. The length of the gap adjust lockout pawl 593 is selected so that it may be extended beyond the transition piece 553 to be received between cog teeth 543 of the gap adjust ring 541. Similarly, the length of the staple lockout pawl 593 is selected so that it may be extended beyond the transition piece 553 to be received between cog teeth 567 of the staple firing ring 561.

In order to render the staple firing ring operational, a user must first lock the gap adjust ring 541 against further rotation by moving the switch beam 595 proximally, thereby moving the lockout beam 592 proximally as well. When in this proximal position with the gap adjust lockout pawl 593 received between the cog teeth 543, the lockout beam 592 prevents further rotation of the gap adjust ring 541 in either direction. When the gap adjust lockout pawl 593 is received between the cog teeth 543, the staple lockout pawl 594 is not received between the cog teeth 567, so that the staple firing ring 561 may be rotated in either direction. In order to render the gap adjust ring 541 operable, a user must first lock the staple firing ring 561 against further rotation by moving the switch beam 595 distally which, in turn, moves the lockout beam 592 distally. When the lockout beam 592 is in this position, the staple firing ring 561 is locked from further rotation in any direction as the staple lockout pawl 594 of the lockout beam 592 is received between cog teeth 567 in the staple firing ring 561 thereby preventing the staple firing ring 561 from further rotation in either direction.

As may be seen in FIGS. 23 and 24, both the gap adjust lockout pawl 593 and the staple lockout pawl 594 may be formed as cantilevered pawls extending outward from the lockout beam 592. The gap adjust lockout pawl 593 and the staple lockout pawl 594 are mounted so that they cam outward away from the lockout beam 592 to ensure secure positioning of the prongs between the cog teeth 543 and 567, respectively.

The disclosed embodiments are illustrative of the various ways in which the present invention may be practiced. Those skilled in the art will recognize that may variations and alternative embodiments may be implemented without departing from the spirit and scope of the present invention.

What is claimed is:

1. A resectioning assembly for controlling operation of a full thickness resection device, comprising:
    a flexible drive shaft;
    a resection actuating mechanism coupled to the flexible drive shaft, the resection actuating mechanism configured to rotate the flexible drive shaft in a first direction;
    a controlling device engaging the flexible drive shaft to control, as the flexible drive shaft rotates in a second direction, a dissipation of torsional energy stored in the flexible drive shaft during rotation in the first direction;
    a full thickness resection device coupled to the flexible drive shaft, the full thickness resection device being driven by rotation of the flexible drive shaft to resect tissue.

2. The resectioning assembly according to claim 1, wherein rotation of the flexible drive shaft in the first direction actuates a tissue stapling mechanism of the full thickness resection device and rotation of the flexible drive shaft in the second direction actuates a tissue cutting mechanism of the full thickness resection device.

3. The resectioning assembly according to claim 2, wherein the resection actuating mechanism in a first mode rotates the flexible drive shaft in the first direction and the resection actuating mechanism in a second mode rotates the flexible drive shaft in the second direction.

4. The resectioning assembly according to claim 1, further comprising a rigid drive shaft coupling the resection actuating mechanism to the flexible drive shaft.

5. The resectioning assembly according to claim 4, wherein the resection actuating mechanism includes a staple-cut knob, and rotating the staple-cut knob in the first direction rotates the rigid drive shaft and the flexible drive shaft in the first direction.

6. The resectioning assembly according to claim 5, wherein the controlling device includes a brake shoe assembly having:
    a clutch engaging and surrounding a portion of the rigid drive shaft;
    a disk engaging and surrounding the clutch,
    a brake pad; and
    a casing rigidly coupled to a body of the resectioning assembly, wherein the clutch and the disk are moveably mounted within the casing and the brake pad is mounted within the casing and configured to act on the disk during rotation of the flexible drive shaft in the second direction.

7. The resectioning assembly according to claim 6, wherein the clutch prevents rotation of the rigid drive shaft in the second direction.

8. The resectioning assembly according to claim 7, wherein the rigid drive shaft rotates inside the clutch in the first direction.

9. The resectioning assembly according to claim 8, wherein rotation of the staple-cut knob in the second direction rotates the rigid drive shaft in the second direction, and rotation of the rigid drive shaft in the second direction engages and rotates the clutch and the disk in the second direction.

10. The resectioning assembly according to claim 9, wherein the disk includes a pawl ring configured to contact the brake pad for during rotation in the second direction of the disk, the clutch, the rigid drive shaft and the flexible drive shaft.

11. The resectioning assembly according to claim 10, wherein the brake pad is mounted within the casing with at least one spring biasing the brake pad towards the pawl ring portion on the disk.

12. The resectioning assembly according to claim 11, wherein the pawl ring portion is oriented on the disk to contact the brake pad at a beginning of the rotation of the disk, the clutch, the rigid drive shaft and the flexible drive shaft in the second direction.

13. The resectioning assembly according to claim 12, wherein at least one of a length and a duration of the contact on the brake pad by the pawl ring portion is determined as a function of an amount of torsional energy stored in the flexible drive shaft during the rotation of the flexible drive shaft in the first direction.

14. The resectioning assembly according to claim 12, wherein the pawl ring portion has a dwell period of a sufficient length to dissipate an amount of torsional energy stored in the flexible drive shaft, the dissipation occurring at a beginning of the rotation in the second direction of the disk, the clutch, the rigid drive shaft and the flexible drive shaft.

15. The resectioning assembly according to claim 14, wherein, after the dwell period has expired, the disk, the clutch, the rigid drive and the flexible drive shaft rotate inside the casing in the second direction substantially free of resistance from the brake pad.

16. The resectioning assembly according to claim 14, wherein, the dwell period has expired, a tissue cutting mechanism coupled to a distal portion of the flexible drive shaft is activated by rotation of the staple-cut knob in the second direction.

17. The resectioning assembly according to claim 16, wherein the controlling device includes a double clutch assembly having a casing, and first and second rotational assemblies moveably mounted within the casing, the first rotational assembly being selectively coupleable to the second rotational assembly, to the casing, and to the rigid drive shaft, the second rotational assembly being coupled to the staple-cut knob and being selectively coupleable to the rigid drive shaft.

18. The resectioning assembly according to claim 17, wherein the first rotational assembly is decoupled from the casing and the second rotational assembly when the first operative procedure is complete.

19. The resectioning assembly according to claim 18, wherein the second rotational assembly includes means for coupling the staple-cut knob to the rigid drive shaft when the staple-cut knob is rotated in the second direction.

20. The resectioning assembly according to claim 17, wherein, when the first rotational assembly is decoupled from the casing and the second rotational assembly, torsional energy stored in the flexible drive shaft is dissipated by an unwinding of the flexible drive shaft and rotation in the second direction of the rigid drive shaft relative to the second rotational assembly.

21. The resectioning assembly according to claim 17, wherein the first rotational assembly includes:
a lockhousing secured to and rotating with the rigid drive shaft;
a pawl ring;
a first clutch resting inside the pawl ring and surrounding and selectively engaging a first portion of the rigid drive shaft to prevent the rigid drive shaft from rotating inside the first clutch in the second direction; and
a ball bearing disposed between an outer surface of the pawl ring and an inner surface of casing of the resectioning assembly selectively coupling the pawl ring and the first clutch to the casing.

22. The resectioning assembly according to claim 21, wherein, when the first rotational assembly is coupled to the second rotational assembly, to the casing and to the rigid drive shaft, rotation of the staple-cut knob in the first direction rotates the second rotational assembly in the first direction and rotates the lockhousing and the rigid drive shaft in the first direction inside the first clutch, wherein the first clutch and the pawl ring remain stationary relative to the rigid drive shaft.

23. The resectioning assembly according to claim 21, wherein the lockhousing includes a decoupling pin decoupling the first rotational assembly from the casing when rotation of the rigid drive shaft and the lockhousing brings the decoupling pin into contact with the ball bearing to move the ball bearing out of a coupling position.

24. The resectioning assembly according to claim 23, wherein the casing includes a decoupling cam decoupling the first rotational assembly from the second rotational assembly by moving the coupling pin out of a coupling position when rotation of the first rotational assembly in the first direction brings the coupling pin into contact with the decoupling cam.

* * * * *